United States Patent
Stump et al.

(10) Patent No.: US 8,778,957 B2
(45) Date of Patent: Jul. 15, 2014

(54) CGRP RECEPTOR ANTAGONISTS

(75) Inventors: Craig A. Stump, Pottstown, PA (US); Amy G. Quigley, Elkins Park, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 261 days.

(21) Appl. No.: 13/256,354

(22) PCT Filed: Mar. 8, 2010

(86) PCT No.: PCT/US2010/026522
§ 371 (c)(1),
(2), (4) Date: Sep. 13, 2011

(87) PCT Pub. No.: WO2010/107605
PCT Pub. Date: Mar. 23, 2010

(65) Prior Publication Data
US 2012/0010193 A1    Jan. 12, 2012

Related U.S. Application Data

(60) Provisional application No. 61/210,413, filed on Mar. 18, 2009.

(51) Int. Cl.
*C07D 471/20* (2006.01)
*A61K 31/437* (2006.01)

(52) U.S. Cl.
USPC .................. 514/278; 546/18; 546/20

(58) Field of Classification Search
USPC ...................... 546/18, 20; 514/278
See application file for complete search history.

(56) References Cited

FOREIGN PATENT DOCUMENTS

| WO | WO 2006/031513 A2 | 3/2006 |
|----|----|----|
| WO | 2007/061695 | 5/2007 |
| WO | 2007/061696 | 5/2007 |
| WO | 2007061692 | 5/2007 |
| WO | 2007061694 | 5/2007 |
| WO | WO 2007/061677 A2 | 5/2007 |
| WO | 2010/021919 | 2/2010 |

OTHER PUBLICATIONS

Stump, Craig A., et. al.; "Identification of potent, highly constrained CGRP Receptor Antagonists", Bioorganic & Medicinal Chemistry Letters, vol. 20, No. 8, Feb. 25, 2010, pp. 2572-2576.
Wood, M.R., et. al.; Novel CGRP Receptor Antagonists through a design strategy of target simplificiation with addition of molecular flexibility:, Bioorganic & Medicinal Chemistry Letters, vol. 19, No. 19, Oct. 1, 2009, pp. 5787-5790.
Supplementary EP Search Report for International App. No. 10753872.0 (PCT/US2011/0026522), 4 pages.
International Search Report (PCT/US2010/26522) for MRL-NOP-00034-US-PCT; mail date Jun. 2, 2010, 3 pages.
Written Opinion (PCT/US2010/26522) for MRL-NOP-00034-US-PCT completed on Apr. 8, 2010, 4 pages.

*Primary Examiner* — Rita Desai
(74) *Attorney, Agent, or Firm* — H. Eric Fischer; John C. Todaro

(57) ABSTRACT

Compounds of Formula (I) (wherein variables $A^1$, $A^2$, $A^3$, ring-B, m, n, J, $E^1$, $E^2$, $E^3$, $R^5$, RPG and Y are as described herein), which are useful as antagonists of CGRP receptors, and useful in the treatment or prevention of diseases in which CGRP receptors are involved, such as headache, and in particular migraine and cluster headache. The invention is also directed to pharmaceutical compositions comprising the compounds of formula (I) and the use of these compounds and compositions in the prevention or treatment of diseases in which CGRP receptors are involved.

(I)

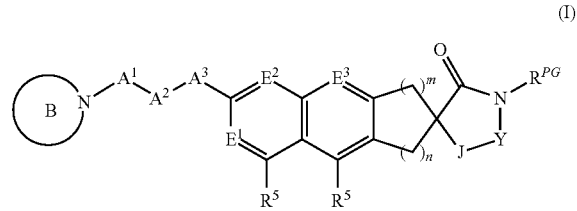

3 Claims, No Drawings

CGRP RECEPTOR ANTAGONISTS

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

Based on pharmacological properties, these receptors are divided into at least two subtypes, denoted $CGRP_1$ and $CGRP_2$. Human α-CGRP-(8-37), a fragment of CGRP that lacks seven N-terminal amino acid residues, is a selective antagonist of $CGRP_1$, whereas the linear analogue of CGRP, diacetoamido methyl cysteine CGRP ([Cys(ACM)2,7] CGRP), is a selective agonist of $CGRP_2$. CGRP is a potent neuromodulator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187), salivary levels of CGRP are elevated in migraine subjects between attacks (Bellamy et al., Headache, 2006, 46, 24-33), and CGRP itself has been shown to trigger migrainous headache (Lassen et al., Cephalalgia, 2002, 22, 54-61). In clinical trials, the CGRP antagonist BIBN4096BS has been shown to be effective in treating acute attacks of migraine (Olesen et al., New Engl. J. Med., 2004, 350, 1104-1110) and was able to prevent headache induced by CGRP infusion in a control group (Petersen et al., Clin. Pharmacol. Ther., 2005, 77, 202-213).

CGRP-mediated activation of the trigeminovascular system may play a key role in migraine pathogenesis. Additionally, CGRP activates receptors on the smooth muscle of intracranial vessels, leading to increased vasodilation, which is thought to contribute to headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura mater in rats increased the diameter of the middle meningeal artery, an effect that was blocked by prior administration of CGRP(8-37), a peptide CGRP antagonist (Williamson et al., Cephalalgia, 1997, 17, 525-531). Trigeminal ganglion stimulation increased facial blood flow in the rat, which was inhibited by CGRP(8-37) (Escott et al., Brain Res. 1995, 669, 93-99). Electrical stimulation of the trigeminal ganglion in marmoset produced an increase in facial blood flow that could be blocked by the non-peptide CGRP antagonist BIBN4096BS (Doods et al., Br. J. Pharmacol., 2000, 129, 420-423). Thus the vascular effects of CGRP may be attenuated, prevented or reversed by a CGRP antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr Opin Inves Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosch et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4(4), 357-358); eye pain (May et al. Cephalalgia, 2002, 22, 195-196), tooth pain (Awawdeh et al., Int. Endocrin. J., 2002, 35, 30-36), non-insulin dependent diabetes mellitus (Molina et al., Diabetes, 1990, 39, 260-265); vascular disorders; inflammation (Zhang et al., Pain, 2001, 89, 265), arthritis, bronchial hyperreactivity, asthma, (Foster et al., Ann. NY Acad. Sci., 1992, 657, 397-404; Schini et al., Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4(4), 357-358); morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); psoriasis; encephalitis, brain trauma, ischaemia, stroke, epilepsy, and neurodegenerative diseases (Rohrenbeck et al., Neurobiol. of Disease 1999, 6, 15-34); skin diseases (Geppetti and Holzer, Eds., Neurogenic Inflammation, 1996, CRC Press, Boca Raton, Fla.), neurogenic cutaneous redness, skin rosaceousness and erythema; tinnitus (Herzog et al., J. Membrane Biology, 2002, 189(3), 225); inflammatory bowel disease, irritable bowel syndrome, (Hoffman et al. Scandinavian Journal of Gastroenterology, 2002, 37(4) 414-422) and cystitis. Of particular importance is the acute or prophylactic treatment of headache, including migraine and cluster headache.

The present invention relates to compounds that are useful as ligands for CGRP receptors, in particular antagonists for CGRP receptors, processes for their preparation, their use in therapy, pharmaceutical compositions comprising them and methods of therapy using them.

SUMMARY OF THE INVENTION

The present invention is directed to compounds of the formula I:

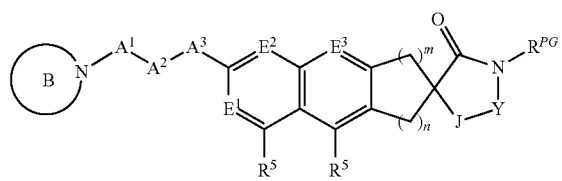

(wherein variables $A^1, A^2, A^3$, ring-B, m, n, J, $E^1, E^2, E^3, R^5$, $R^{PG}$ and Y are as described herein) which are antagonists of CGRP receptors and which are useful in the treatment or prevention of diseases in which the CGRP is involved, such as migraine. The invention is also directed to pharmaceutical compositions comprising these compounds and the use of these compounds and compositions in the prevention or treatment of such diseases in which CGRP is involved.

DETAILED DESCRIPTION OF THE INVENTION

The present invention is directed to compounds of the formula I:

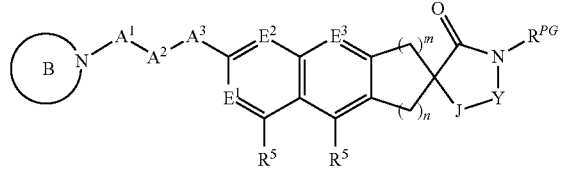

wherein:
$E^1$, $E^2$, and $E^3$ are selected from:
 (1) =N—,
 (2) =N$^+$(O$^-$)—, and
 (3) =C(R$^5$)—;
$A^1$, $A^2$ and $A^3$ are each independently selected from:
 (1) a bond,
 (2) —CR$^1$R$^2$—,
 (3) —NR$^b$—,
 (4) —CR$^1$R$^2$—NR$^b$—,
 (5) —CR$^1$R$^2$—CH$_2$—,
 (6) —O—CR$^1$R$^2$—,
 (7) —CR$^1$R$^2$—O—, and
 (8) —C(=O)—;
 provided that at least one of $A^1$, $A^2$ and $A^3$ is not a bond;
$R^1$ and $R^2$ are each independently selected from:
 (1) hydrogen,
 (2) $C_{1-6}$ alkyl, which is unsubstituted or substituted with 1-5 substituents each independently selected from:
   (a) —$C_{3-6}$cycloalkyl, which is unsubstituted or substituted with 1-5 halo,
   (b) —OR$^a$,
   (c) halo, and
   (d) phenyl, which is unsubstituted or substituted with 1-5 halo,
 (3) —OR$^a$,
 (4) halo, and
 (5) phenyl or pyridinyl, which is unsubstituted or substituted with 1-5 substituents each independently selected from:
   (a) halo,
   (b) —OR$^a$,
   (c) —CN, and
   (d) —$C_{1-6}$alkyl, which is unsubstituted or substituted with 1-5 halo;
$R^5$ is independently selected from:
 (1) hydrogen
 (2) —$C_{1-6}$alkyl, which is unsubstituted or substituted with 1-6 halo,
 (3) halo,
 (4) —OR$^a$, and
 (5) —CN;
B is a heterocycle selected from the group consisting of:

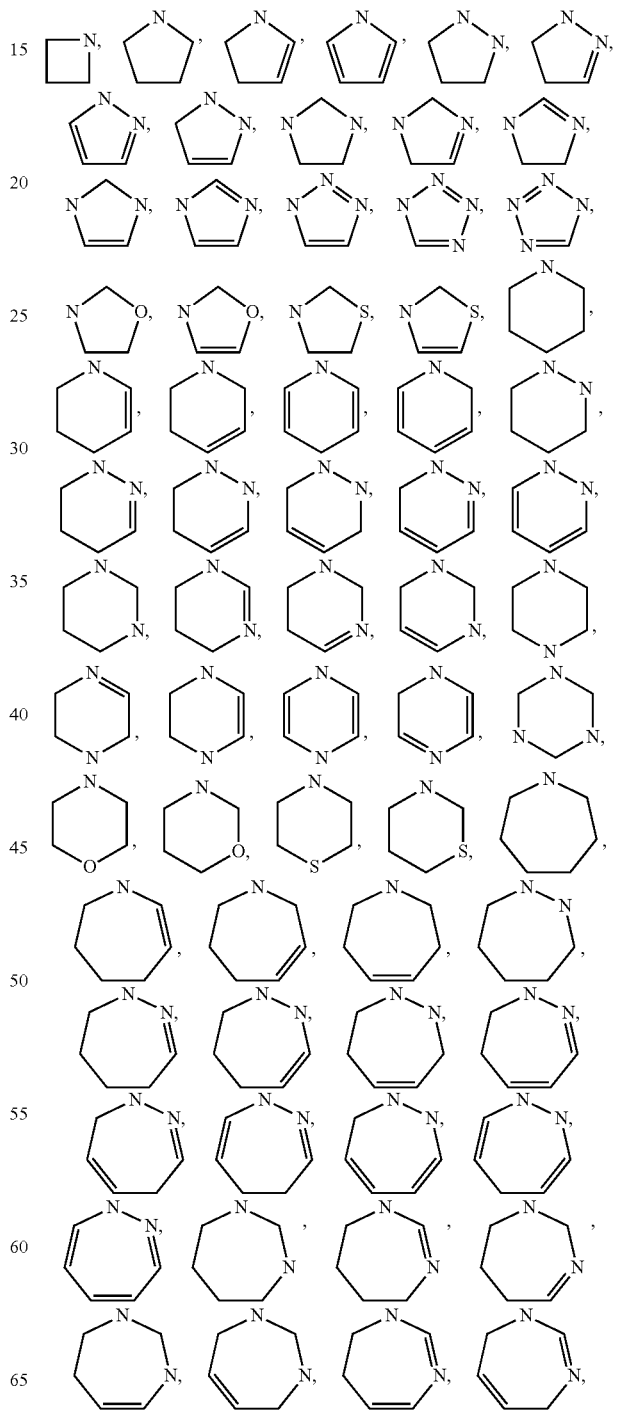

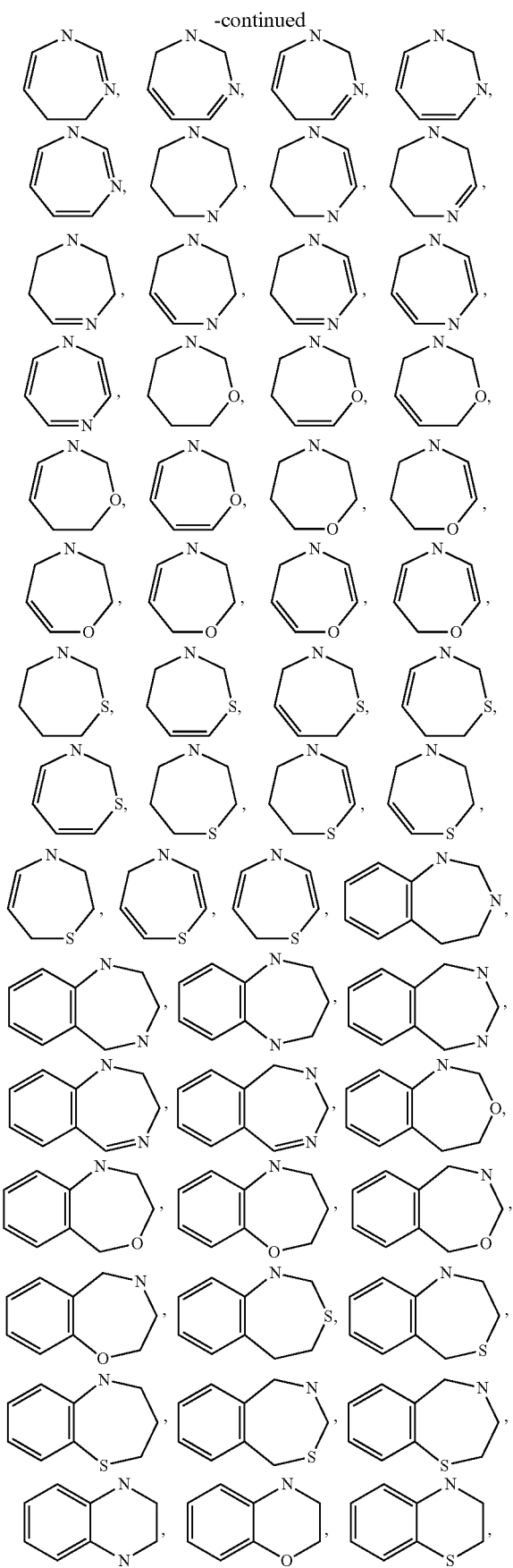
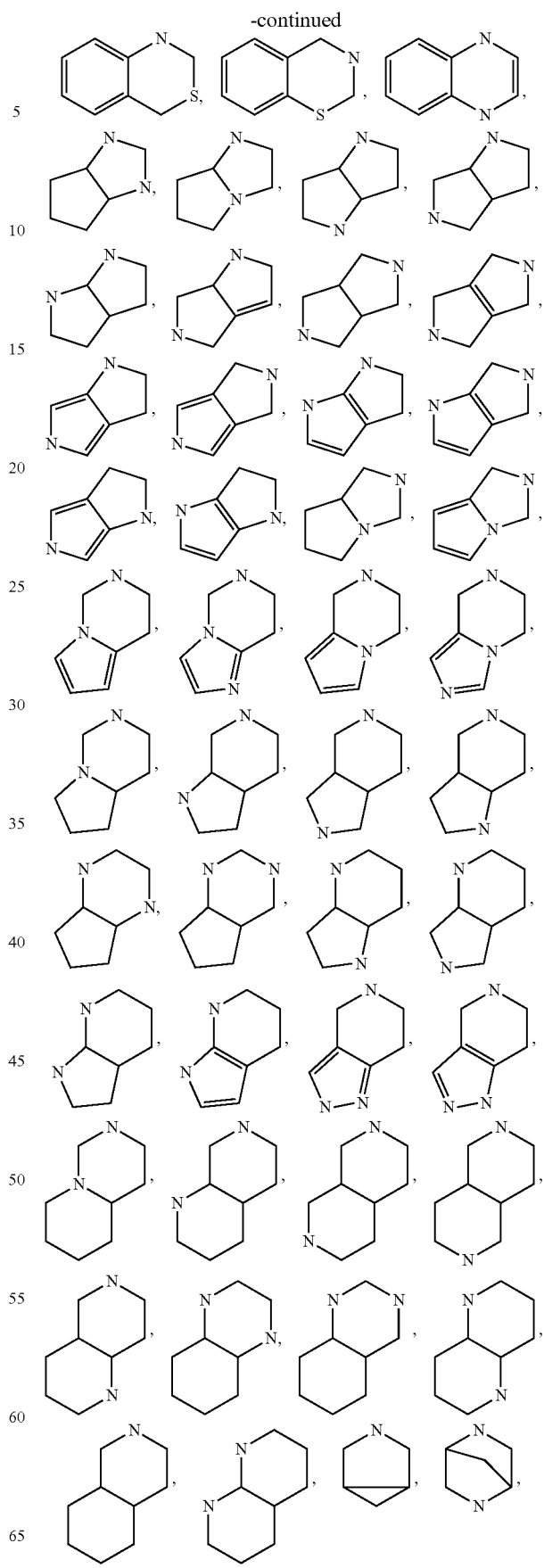

-continued where B is linked to A¹ via a nitrogen atom in 13 and where B is unsubstituted or substituted with 1-6 substituents independently selected from $R^3$, $R^4$, $R^6$, $R^7$, $R^8$ and $R^9$;

$R^3$, $R^4$, $R^6$, $R^7$, $R^8$ and $R^9$ are each independently selected from:
(1) hydrogen,
(2) —$C_{1-6}$alkyl, which is unsubstituted or substituted with 1-5 substituents each independently selected from:
  (a) halo,
  (b) —$OR^a$,
  (c) —$C_{3-6}$cycloalkyl,
  (d) phenyl or heterocycle, wherein said heterocycle is selected from: benzodioxolyl, imidazolyl, indolyl, pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from
    (i) halo,
    (ii) —$C_{1-6}$alkyl, which is unsubstituted or substituted with 1-5 halo,
    (iii) —$OR^a$, and
    (iv) —CN
  (e) —$CO_2R^a$,
  (f) —$C(=O)NR^bR^c$,
  (g) —$S(O)_vR^d$,
  (h) —CN,
  (i) —$NR^bR^c$,
  (j) —$N(R^b)C(=O)R^a$,
  (k) —$N(R^b)SO_2R^d$,
  (l) —$CF_3$,
  (m) —O—$CO_2R^d$,
  (n) —O—(C=O)—$NR^bR^c$,
  (o) —$NR^b$—(C=O)—$NR^bR^c$, and
  (p) —$C(=O)R^a$,
(3) —$C_{3-6}$cycloalkyl, which is unsubstituted or substituted with 1-5 substituents each independently selected from:
  (a) halo,
  (b) —CN,
  (e) —$C_{1-6}$alkyl, which is unsubstituted or substituted with 1-5 halo,
  (d) —$OR^a$, and
  (e) phenyl, which is unsubstituted or substituted with 1-5 substituents each independently selected from:
    (i) —$OR^a$,
    (ii) halo,
    (iii) —CN, and
    (iv) —$C_{1-6}$alkyl, which is unsubstituted or substituted with 1-5 halo,
(4) phenyl or heterocycle, wherein said heterocycle is selected from: benzimidazolyl, benzoxazinyl, benzoxazolyl, indanyl, indolyl, morpholinyl, oxadiazolyl, oxazolyl, pyridyl, pyrimidinyl, pyrazinyl, pyrazolyl, pyridazinyl, piperidinyl, piperazinyl, pyrrolidinyl, thienyl, tetrazolyl, thiazolyl, and triazolyl, which phenyl or heterocycle is unsubstituted or substituted with 1-5 substituents each independently selected from:
  (a) halo,
  (b) —$OR^a$,
  (c) —$C_{3-6}$cycloalkyl,
  (d) phenyl or pyridyl, which is unsubstituted or substituted with 1-5 substituents each independently selected from:
    (i) halo,
    (ii) which is unsubstituted or substituted with 1-6 halo, and
    (iii) —$OR^a$,
  (e) —$CO_2R^a$,
  (f) —$C(=O)NR^bR^c$,
  (g) —$S(O)_vR^d$,
  (h) —CN,
  (i) —$NR^bR^c$,
  (j) —$N(R^b)C(=O)R^a$,
  (k) —$N(R^b)SO_2R^d$,
  (l) —O—$CO_2R^d$,
  (m) —O—(C=O)—$NR^bR^c$,
  (n) —$NR^b$—(C=O)—$NR^bR^c$,
  (o) oxo,
  (p) —$C(=O)R^a$, and
  (q) —$C_{1-6}$alkyl, which is unsubstituted or substituted with 1-6 halo,
(5) halo,
(6) oxo,
(7) —$OR^a$,
(8) —CN,
(9) —$CO_2R^a$,
(10) —$C(=O)R^a$,
(11) —$NR^bR^c$,
(12) —$S(O)_vR^d$,
(13) —$C(=O)NR^bR^c$,
(14) —O—(C=O)$R^a$,
(15) —O—$CO_2R^d$,
(16) —$N(R^b)CO_2R^d$,
(17) —O—(C=O)—$NR^bR^c$,
(18) —$NR^b$—(C=O)—$NR^bR^c$,
(19) —$SO_2NR^bR^c$, and
(20) —$N(R^b)SO_2R^d$,
or $R^7$ and $R^8$ and the atom(s) to which they are attached join to form a ring selected from azetidinyl, aziridinyl, cyclobutyl, cycloheptyl, cyclohexyl, cyclooctyl, cyclopentyl, cyclopropyl, dihydrobenzofuranyl, dihydrobenzopyranyl, dioxanyl, dioxoalanyl, indanyl, indanyl, indolinyl, isoindolinyl, morpholinyl, oxetanyl, piperazinyl, piperidinyl, pyrrolidinyl, tetrahydrofuranyl, tetrahydroisoquinolinyl, tetrahydronaphthyl, tetrahydroquinolinyl, tetrahydropyranyl, tetrahydrothiapyranyl, tetrahydrothienyl, thiamorpholinyl, and thietanyl, wherein the sulfur is optionally oxidized to the sulfone or sulfoxide, which ring is unsubstituted or substituted with 1-5 substituents each independently selected from:
- (a) —$C_{1-6}$alkyl, which is unsubstituted or substituted with 1-3 substituents each independently selected from:
  - (i) halo,
  - (ii) —$OR^a$,
  - (iii) —$C_{3-6}$cycloalkyl,
  - (iv) —$CO_2R^a$,
  - (v) —$NR^bR^c$,
  - (vi) —$S(O)_vR^d$,
  - (vii) —$C(=O)NR^bR^c$, and
  - (viii) phenyl, which is unsubstituted or substituted with 1-5 halo,
- (b) phenyl or heterocycle, wherein heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, wherein the phenyl or heterocycle is optionally fused to the ring, and which phenyl or heterocycle is unsubstituted or substituted with 1-5 substituents each independently selected from:
  - (i) halo,
  - (ii) —$C_{1-6}$alkyl, which is unsubstituted or substituted with 1-5 halo, and
  - (iii) —$OR^a$,
- (c) —$OR^a$,
- (d) halo,
- (e) —$CO_2R^a$,
- (f) —$C(=O)NR^bR^c$,
- (g) —$S(O)_vR^d$,
- (h) —CN,
- (i) —$NR^bR^c$,
- (j) —$N(R^b)C(=O)R^a$,
- (k) —$N(R^b)SO_2R^d$,
- (l) —O—(C=O)$R^a$,
- (m) —O—$CO_2R^d$,
- (n) —O—(C=O)—$NR^bR^c$,
- (o) —$NR^b$—(C=O)—$NR^bR^b$,
- (p) —$C(=O)R^a$, and
- (q) oxo;

$R^{PG}$ is independently selected from:
(1) hydrogen,
(2) —$C_{1-6}$alkyl which is unsubstituted or substituted with 1-5 halo,
(3) —$CH_2OR^a$,
(4) —$CH_2$—O—$CH_2CH_2Si(CH_3)_3$,
(5) —$(CH_2)_k$-phenyl, which is unsubstituted or substituted with 1-3 substituents each independently selected from:
  (a) halo,
  (b) —$OR^a$,
  (c) —CN, and
  (d) —$C_{1-6}$alkyl, which is unsubstituted or substituted with 1-6 halo;

J is independently selected from:
(1) =$C(R^{16a})$—,
(2) —$CR^{17}R^{18}$—,
(3) —C(=O)—,
(4) =N—, and
(5) —$N(R^b)$—;

Y is independently selected from:
(1) =$C(R^{16b})$—,
(2) —$CR^{17}R^{18}$—,
(3) —C(=O)—,
(4) =N—, and
(5) —$N(R^{16b})$—;

$R^{17}$ and $R^{18}$ are each independently selected from:
(1) hydrogen,
(2) halo,
(3) —$OR^a$,
(4) —$C_{1-6}$alkyl, which is unsubstituted or substituted with 1-4 substituents each independently selected from:
  (a) halo,
  (b) —$OR^a$,
  (c) —CN,
  (d) phenyl or heterocycle, wherein said heterocycle is selected from pyridyl, pyrimidinyl, thienyl, pyridazinyl, piperidinyl, azetidinyl, piperazinyl, pyrrolidinyl, morpholinyl, tetrahydrofuranyl, tetrahydropyranyl and pyrazinyl, which phenyl or heterocycle is unsubstituted or substituted with 1-5 substituents each independently selected from:
    (i) —$OR^a$,
    (ii) halo,
    (iii) —CN,
    (iv) —$C_{1-6}$alkyl which is unsubstituted or substituted with 1-6 halo,
(5) phenyl or heterocycle wherein heterocycle is selected from pyridyl, pyrimidinyl, thienyl, pyridazinyl, piperidinyl, azetidinyl, piperazinyl, pyrrolidinyl, morpholinyl, tetrahydrofuranyl, tetrahydropyranyl and pyrazinyl, which phenyl or heterocycle is unsubstituted or substituted with 1-5 substituents each independently selected from:
  (a) halo,
  (b) —CN,
  (e) —$OR^a$,
  (d) nitro,
  (e) —$C_{1-6}$alkyl which is unsubstituted or substituted with 1-6 halo;

or $R^{17}$ and $R^{18}$ and the atom to which they are attached join to form a 4-, 5-, or 6-membered ring optionally containing a heteroatom selected from N, O, and S, wherein the sulfur is optionally oxidized to the sulfone or sulfoxide, which ring is unsubstituted or substituted with 1-4 substituents each independently selected from:
  (a) halo,
  (b) —$OR^a$,
  (c) —$C_{1-6}$alkyl, which is unsubstituted or substituted with 1-6 halo, and
  (d) phenyl, which is unsubstituted or substituted with 1-6 halo;

$R^{16a}$ and $R^{16b}$ are each independently selected from:
(1) hydrogen,
(2) —$C_{1-4}$alkyl, which is unsubstituted or substituted with 1-5 substituents each independently selected from:
  (a) halo,
  (b) —$OR^a$,
  (c) —$C_{3-6}$cycloalkyl,
  (d) phenyl or heterocycle, wherein said heterocycle is selected from: imidazolyl, oxazolyl, pyridyl, pyrimidinyl, pyrazinyl, pyridazinyl, piperidinyl, piperazinyl, pyrrolidinyl, thiazolyl, thienyl, triazolyl, isoxazolyl and morpholinyl, which phenyl or heterocycle is unsubstituted or substituted with 1-3 substituents each independently selected from:
  (i) halo,
  (ii) —OR$^a$,
  (iii) —CN, and
  (iv) —C$_{1-6}$alkyl, which is unsubstituted or substituted with 1-6 halo,
(3) phenyl or heterocycle, wherein heterocycle is selected from: imidazolyl, oxazolyl, pyridyl, pyrimidinyl, pyrazinyl, pyridazinyl, tetrahydrofuryl, piperidinyl, piperazinyl, pyrrolidinyl, azetidinyl, thiazolyl, thienyl, triazolyl, isoxazolyl and morpholinyl, which phenyl or heterocycle is unsubstituted or substituted with 1-3 substituents each independently selected from:
  (a) halo,
  (b) —OR$^a$,
  (c) —C$_{3-6}$cycloalkyl,
  (d) —C$_{1-4}$alkyl which is unsubstituted or substituted with 1-6 halo, and
  (e) phenyl, which is unsubstituted or substituted with 1-5 substituents each independently selected from:
    (i) halo,
    (ii) —C$_{1-6}$alkyl, which is unsubstituted or substituted with 1-6 halo, and
    (iii) —OR$^a$,
(4) halo,
(5) —OR$^a$,
(6) —CN,
(7) —CO$_2$R$^a$,
(8) —NR$^b$R$^c$, and
(9) —C(=O)NR$^b$R$^c$,
or R$^{16a}$ and R$^{16b}$ and the atom(s) to which they are attached join to form a ring selected from cyclopentenyl, cyclohexenyl, phenyl, pyridyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl and dihydrothiopyranyl, which ring is unsubstituted or substituted with 1-5 substituents each independently selected from:
  (a) —C$_{1-6}$alkyl, which is unsubstituted or substituted with 1-3 substituents each independently selected from:
    (i) halo,
    (ii) —OR$^a$,
    (iii) —C$_{3-6}$cycloalkyl,
    (iv) phenyl or heterocycle, wherein heterocycle is selected from pyridyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from:
      (I) —OR$^a$,
      (II) halo,
      (III) —CN, and
      (IV) —C$_{1-6}$alkyl which is unsubstituted or substituted with 1-6 halo,
    (v) —CO$_2$R$^a$,
    (vi) —NR$^b$R$^c$,
    (vii) —S(O)$_v$R$^d$,
    (viii) —C(=O)NR$^b$R$^c$,
    (ix) —N(R$^b$)CO$_2$R$^a$, and
    (x) —N(R$^b$)SO$_2$R$^d$,
  (b) phenyl or heterocycle, wherein said heterocycle is selected from pyridyl, pyrimidinyl, pyrazinyl, pyridazinyl, piperidinyl, azetidinyl, piperazinyl, pyrrolidinyl, thienyl and morpholinyl, which phenyl or heterocycle is unsubstituted or substituted with 1-5 substituents each independently selected from:
    (i) halo,
    (ii) —OR$^a$,
    (iii) —CN, and
    (iv) —C$_{1-6}$alkyl which is unsubstituted or substituted with 1-6 halo,
  (c) halo,
  (d) —S(O)$_v$R$^d$,
  (e) —OR$^a$,
  (f) —CN,
  (g) —C(=O)R$^a$,
  (h) —NR$^b$R$^c$,
  (i) —C(=O)NR$^b$R$^c$,
  (j) —CO$_2$R$^a$,
  (k) —(NR$^b$)CO$_2$R$^a$,
  (l) —O—(C=O)—NR$^b$R$^c$,
  (m) —(NR$^b$))—(C=O)—NR$^b$R$^c$,
  (n) oxo, and
  (o) —(NR$^b$)SO$_2$R$^d$;
R$^a$ is independently selected from:
  (1) hydrogen,
  (2) C$_{1-6}$alkyl, which is unsubstituted or substituted with 1-7 substituents each independently selected from:
    (a) halo,
    (b) —O—C$_{1-6}$alkyl, which is unsubstituted or substituted with 1-6 halo,
    (c) hydroxyl,
    (d) —C(=O)—O—C$_{1-6}$alkyl, which is unsubstituted or substituted with 1-6 halo,
    (e) —CN, and
    (f) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
      (i) halo,
      (ii) —O—C$_{1-6}$alkyl, which is unsubstituted or substituted with 1-6 halo,
      (iii) —CN,
      (iv) nitro,
      (v) hydroxyl, and
      (vi) —C$_{1-6}$alkyl, which is unsubstituted or substituted with 1-6 halo,
  (3) phenyl or heterocycle wherein said heterocycle is selected from pyridyl, indolyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
    (a) halo,
    (b) —CN,
    (c) —O—C$_{1-6}$alkyl, which is unsubstituted or substituted with 1-6 halo,
    (d) nitro,
    (e) hydroxyl, and
    (f) —C$_{1-6}$alkyl, which is unsubstituted or substituted with 1-6 halo, and
  (4) —C$_{3-6}$cycloalkyl, which is unsubstituted or substituted with 1-6 halo;
R$^b$ and R$^c$ are independently selected from:
  (1) hydrogen,
  (2) C$_{1-6}$alkyl, which is unsubstituted or substituted with 1-7 substituents each independently selected from:

(a) halo,
(b) —OR$^a$,
(c) —CN,
(d) —CO$_2$R$^a$,
(e) phenyl or heterocycle, wherein said heterocycle is selected from pyridyl, pyrimidinyl, thienyl, pyridazinyl, piperidinyl, azetidinyl, (uranyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
  (i) halo,
  (ii) —OR$^a$,
  (iii) —C$_{1-6}$alkyl, which is unsubstituted or substituted with 1-6 halo, and
  (iv) nitro,
(3) phenyl or heterocycle, wherein said heterocycle is selected from pyridyl, pyrimidinyl, thienyl, pyridazinyl, piperidinyl, azetidinyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
  (a) halo,
  (b) —OR$^a$,
  (c) —C$_{1-6}$alkyl, which is unsubstituted or substituted with 1-6 halo,
  (d) —C$_{3-6}$cycloalkyl, which is unsubstituted or substituted with 1-6 halo,
  (e) —CN, and
  (f) —CO$_2$R$^a$,
(4) —C$_{3-6}$cycloalkyl, which is unsubstituted or substituted with 1-6 halo; or R$^b$ and R$^c$ and the nitrogen to which they are attached join to form a 4-, 5-, or 6-membered ring optionally containing an additional heteroatom selected from N, O, and S, wherein the sulfur is optionally oxidized to the sulfone or sulfoxide, which ring is unsubstituted or substituted with 1-4 substituents each independently selected from
  (a) halo,
  (b) —OR$^a$, and
  (c) —C$_{1-6}$alkyl, which is unsubstituted or substituted with 1-6 halo, and
  (d) phenyl;
R$^d$ is independently selected from:
(1) C$_{1-6}$alkyl, which is unsubstituted or substituted with 1-7 substituents each independently selected from:
  (a) halo,
  (b) —OR$^a$,
  (c) —CO$_2$R$^a$
  (d) —CN, and
  (e) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
    (i) halo,
    (ii) —OR$^a$,
    (iii) —CN,
    (iv) nitro, and
    (v) —C$_{1-6}$alkyl, which is unsubstituted or substituted with 1-6 halo,
(2) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
  (a) halo,
  (b) —OR$^a$,
  (c) —C$_{1-6}$alkyl, which is unsubstituted or substituted with 1-6 halo,
  (d) —C$_{3-6}$cycloalkyl, which is unsubstituted or substituted with 1-6 halo
  (e) nitro,
  (f) —CN, and
  (g) —CO$_2$R$^a$,
(3) —C$_{3-6}$cycloalkyl, which is unsubstituted or substituted with 1-6 halo;
m is 1, 2, or 3;
n is 1, 2, or 3;
v is 0, 1, or 2;
k is 0, 1, or 2;
and pharmaceutically acceptable salts thereof and tautomers thereof and individual enantiomers and diastereomers thereof.

In particular embodiments of the compounds of formula (I), E$^1$ and E$^3$ are =C(R$^5$)—. In these embodiments, typically each R$^5$ is hydrogen.

In particular embodiments of the compounds of formula (I), A$^2$ and A$^3$ are each a bond, and A$^1$ is selected from the group consisting of
(1) —CR$^1$R$^2$—,
(2) —NR$^b$—,
(3) —CR$^1$R$^2$—NR$^b$—,
(4) —CR$^1$R$^2$—CH$_2$—,
(5) —O—CR$^1$R$^2$—,
(6) —CR$^1$R$^2$—O—, and
(7) —C(=O)—.

In these embodiments, typically A$^1$ is —CR$^1$R$^2$—, and R$^1$ and R$^2$ are typically both hydrogen.

In these embodiments, alternatively A$^1$ is —C(=O)—.

In particular embodiments of the compounds of formula (I), B is selected from the group consisting of

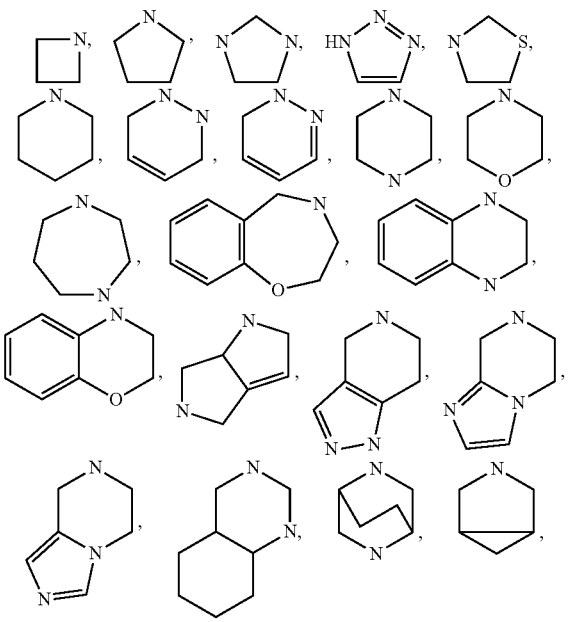

-continued

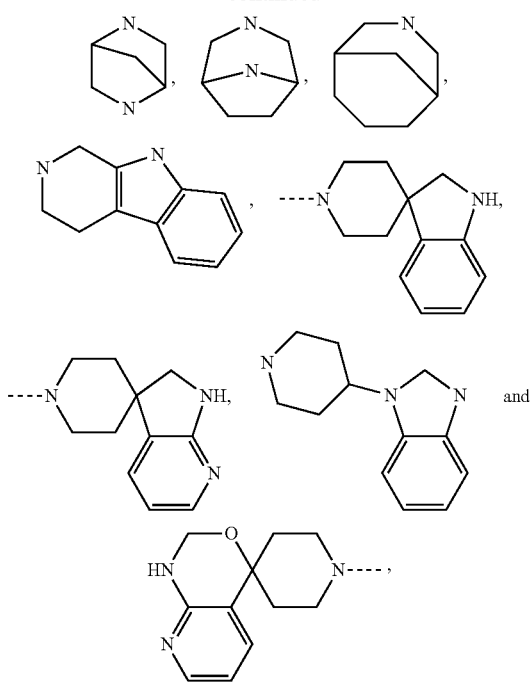

wherein B is unsubstituted or substituted with 1-6 substitutents independently selected from $R^3$, $R^4$, $R^6$, $R^7$, $R^8$ and $R^9$.

In particular embodiments, B is selected from the group consisting of

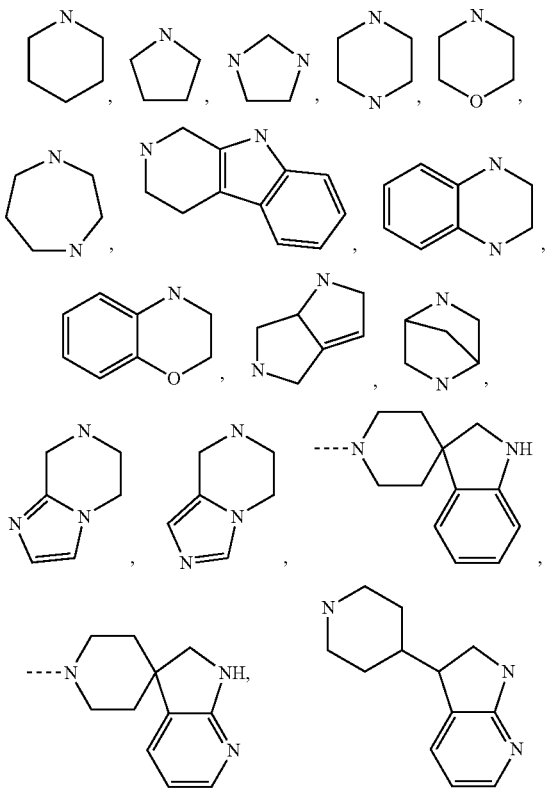

-continued

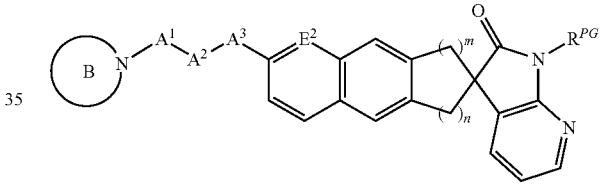

wherein B is unsubstituted or substituted with 1-6 substitutents independently selected from $R^3$, $R^4$, $R^6$, $R^7$, $R^8$ and $R^9$.

In particular embodiments of the compounds of formula (I), $R^{PG}$ is hydrogen.

In particular embodiments of the compounds of formula (I), m and n are each 1.

In particular embodiments of the compounds of formula (I), J is $=C(R^{16a})-$ and Y is $=C(R^{16b})-$, and $R^{16a}$ and $R^{16b}$ and the atom(s) to which they are attached join to form a ring selected from cyclopentenyl, cyclohexenyl, phenyl and pyridyl, wherein the ring is optionally substituted as described above. Typically, $R^{16a}$ and $R^{16b}$ are linked together to form an unsubstituted pyridyl ring.

In particular embodiments of the compounds of formula (I), J is $-N(R^b)-$ and Y is $=C(=O)-$, and $R^b$ is selected from hydrogen or $-C_{1-6}$alkyl, which is unsubstituted or substituted with 1-3 halo. Typically, $R^b$ is methyl.

In one embodiment of the invention, the compounds of formula (I) are compounds of formula (II)

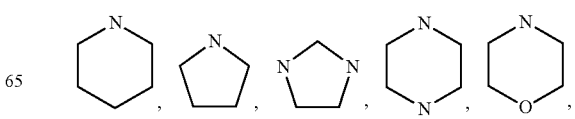

and pharmaceutically acceptable salts thereof and tautomers thereof and individual enantiomers and diastereomers thereof, wherein variables $A^1$, $A^2$, $A^3$, ring-B, m, n, $E^2$, and $R^{PG}$ are as described herein.

In one embodiment of the compounds of formula (II), $A^2$ and $A^3$ are each a bond, and $A^1$ is selected from the group consisting of (1) $-CR^1R^2-$, (2) $-NR^b-$, (3) $-CR^1R^2-NR^b-$, (4) $-CR^1R^2-CH_2-$, (5) $-O-CR^1R^2-$, (6) $-CR^1R^2-O-$, and (7) $-C(=O)-$.

Typically, in this embodiment, $A^1$ is $-CR^1R^2-$, and wherein $R^1$ and $R^2$ are typically both hydrogen, or $A^1$ is $-C(=O)-$.

In particular embodiments of the compounds of formula (II), B is selected from the group consisting of -continued

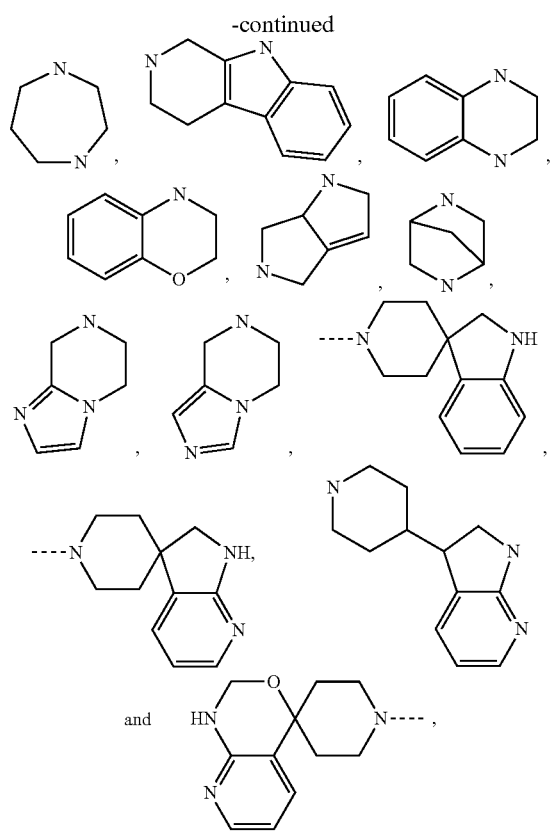

wherein B is unsubstituted or substituted with 1-6 substitutents independently selected from $R^3$, $R^4$, $R^6$, $R^7$, $R^8$ and $R^9$.

In particular embodiments of the compounds of formula (II), $R^{PG}$ is hydrogen.

In particular embodiments of the compounds of formula (II), m and n are each 1.

In particular embodiments of the compounds of formula (II), $E^2$ is nitrogen.

In one embodiment of the invention, the compounds of formula (I) are compounds of formula (III)

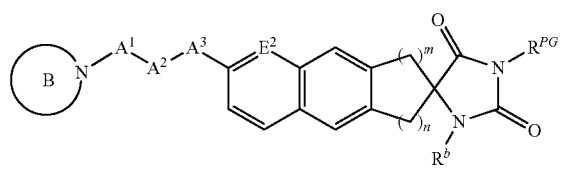

and pharmaceutically acceptable salts thereof and tautomers thereof and individual enantiomers and diastereomers thereof, wherein variables $A^1$, $A^2$, $A^3$, ring-B, m, n, $E^2$, $R^b$ and $R^{PG}$ are as described herein.

In one embodiment of the compounds of formula (III), $A^2$ and $A^3$ are each a bond, and $A^1$ is selected from the group consisting of
(1) —$CR^1R^2$—,
(2) —$NR^b$—,
(3) —$CR^1R^2$—$NR^b$—,
(4) —$CR^1R^2$—$CH_2$—,
(5) —O—$CR^1R^2$—,
(6) —$CR^1R^2$—O—, and
(7) —C(=O)—.

Typically, in this embodiment, $A^1$ is —$CR^1R^2$—, and wherein $R^1$ and $R^2$ are typically both hydrogen, or $A^1$ is —C(=O)—.

In particular embodiments of the compounds of formula (III), B is selected from the group consisting of

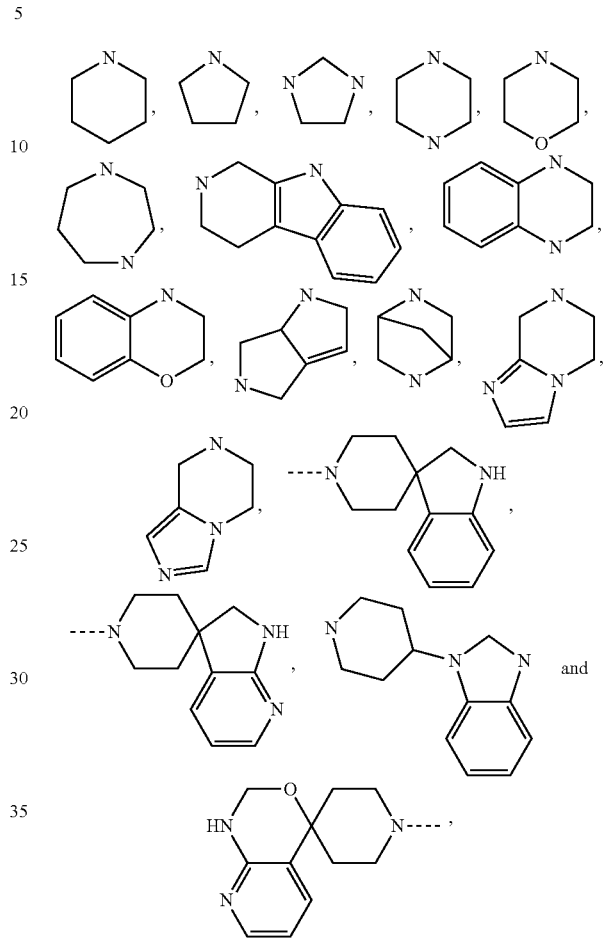

wherein B is unsubstituted or substituted with 1-6 substitutents independently selected from $R^3$, $R^4$, $R^6$, $R^7$, $R^8$ and $R^9$.

In particular embodiments of the compounds of formula (III), $R^{PG}$ is hydrogen.

In particular embodiments of the compounds of formula (III), $R^b$ is hydrogen or methyl.

In particular embodiments of the compounds of formula (III), m and n are each 1.

In particular embodiments of the compounds of formula (III), $E^2$ is nitrogen.

In one embodiment of the invention, the compounds of formula (I) are compounds of formula (IV)

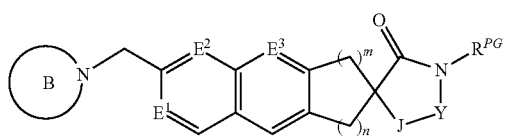

and pharmaceutically acceptable salts thereof and tautomers thereof and individual enantiomers and diastereomers thereof, wherein variables ring-B, m, n, J, Y, $E^1$, $E^2$, $E^3$, and $R^{PG}$ are as described herein.

In particular embodiments of the compounds of formula (IV), B is selected from the group consisting of

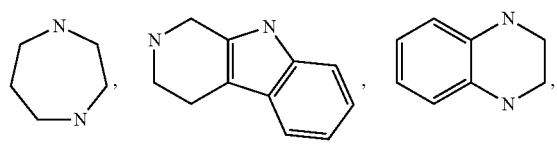

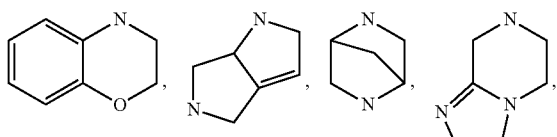

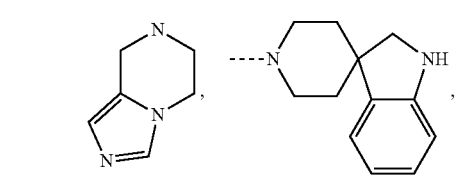

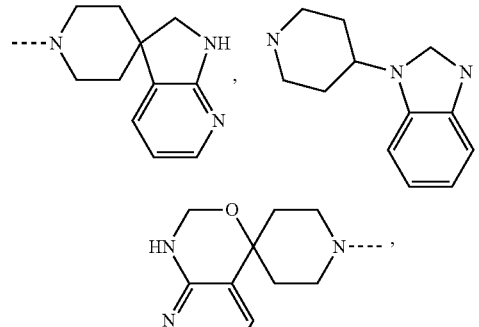

wherein B is unsubstituted or substituted with 1-6 substitutents independently selected from $R^3$, $R^4$, $R^6$, $R^7$, $R^8$ and $R^9$.

In particular embodiments of the compounds of formula (IV), $R^{PG}$ is hydrogen.

In particular embodiments of the compounds of formula (IV), m and n are each 1.

In particular embodiments of the compounds of formula (IV), $E^2$ is nitrogen and $E^1$ and $E^3$ are =C($R^5$)—, wherein $R^5$ may be hydrogen.

In particular embodiments of the compounds of formula (IV), J is =C($R^{16a}$)— and Y is =C($R^{16b}$)—, and or $R^{16a}$ and $R^{16b}$ and the atom(s) to which they are attached join to form a ring selected from cyclopentenyl, cyclohexenyl, phenyl and pyridyl, wherein the ring is optionally substituted as described above. Typically, $R^{16a}$ and $R^{16b}$ are linked together to form an unsubstituted pyridyl ring.

In particular embodiments of the compounds of formula (IV), J is —N($R^b$)— and Y is =C(=O)—, and $R^b$ is selected from hydrogen or —$C_{1-6}$alkyl, which is unsubstituted or substituted with 1-3 halo. Typically, $R^b$ is methyl.

In one embodiment of the invention, the compounds of formula (I) are compounds of formula (V)

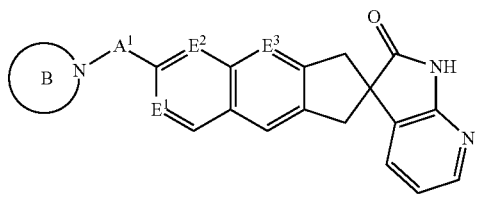

and pharmaceutically acceptable salts thereof and tautomers thereof and individual enantiomers and diastereomers thereof, wherein variables $A^1$, ring-B, $E^1$, $E^2$, and $E^3$ are as described herein.

In one embodiment of the compounds of formula (V), $A^1$ is selected from the group consisting of
(1) —$CR^1R^2$—,
(2) —$NR^b$—,
(3) —$CR^1R^2$—$NR^b$—,
(4) —$CR^1R^2$—$CH_2$—,
(5) —O—$CR^1R^2$—,
(6) —$CR^1R^2$—O—, and
(7) —C(=O)—.

Typically, in this embodiment, $A^1$ is —$CR^1R^2$—, and wherein $R^1$ and $R^2$ are typically both hydrogen, or $A^1$ is —C(=O)—.

In particular embodiments of the compounds of formula (V), B is selected from the group consisting of

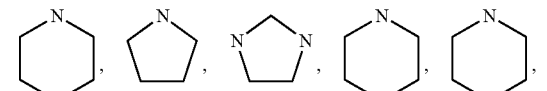

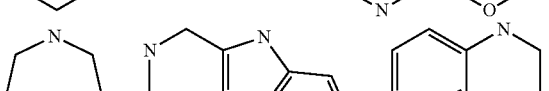

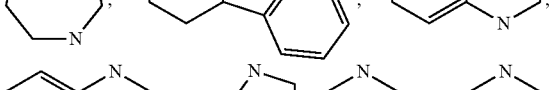

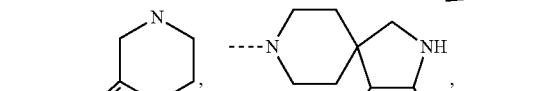

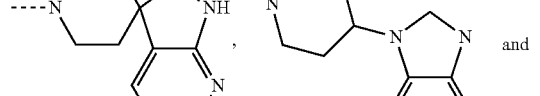

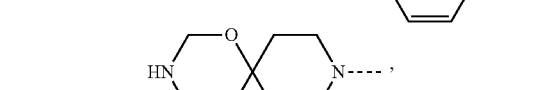

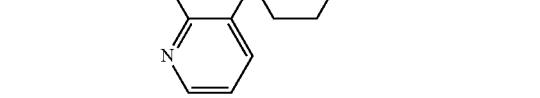

wherein B is unsubstituted or substituted with 1-6 substitutents independently selected from $R^3$, $R^4$, $R^6$, $R^7$, $R^8$ and $R^9$.

In particular embodiments of the compounds of formula (V), $E^2$ is nitrogen and $E^1$ and $E^3$ is $=C(R^5)-$, wherein $R^5$ is suitably hydrogen.

In one embodiment of the invention, the compounds of formula (I) are compounds of formula (VI)

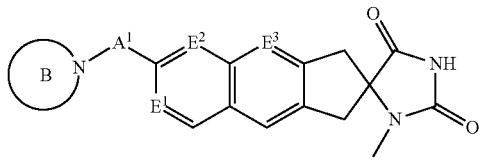

and pharmaceutically acceptable salts thereof and tautomers thereof and individual enantiomers and diastereomers thereof, wherein variables $A^1$, ring-B, $E^1$, $E^2$, and $E^3$ are as described herein.

In one embodiment of the compounds of formula (VI), $A^1$ is selected from the group consisting of (1) $-CR^1R^2-$,
(2) $-NR^b-$,
(3) $-CR^1R^2-NR^b-$,
(4) $-CR^1R^2-CH_2-$,
(5) $-O-CR^1R^2-$,
(6) $-CR^1R^2-O-$, and
(7) $-C(=O)-$.

Typically, in this embodiment, $A^1$ is $-CR^1R^2-$, and wherein $R^1$ and $R^2$ are typically both hydrogen, or $A^1$ is $-C(=O)-$.

In particular embodiments of the compounds of formula (VI), B is selected from the group consisting of

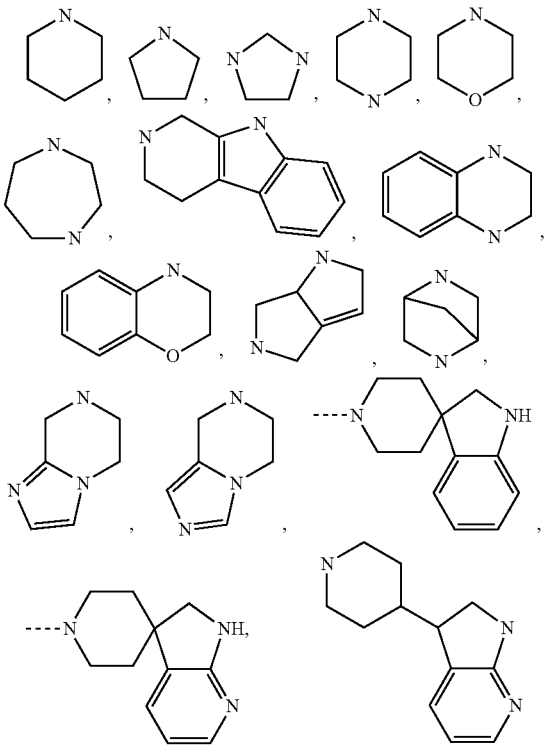

wherein B is unsubstituted or substituted with 1-6 substitutents independently selected from $R^3$, $R^4$, $R^6$, $R^7$, $R^8$ and $R^9$.

In particular embodiments of the compounds of formula (VI), $E^2$ is nitrogen and $E^1$ and $E^3$ is $=C(R^5)-$, wherein $R^5$ is suitably hydrogen.

The present invention is further directed to the exemplary compounds 1-210 of formula (I), and pharmaceutically acceptable salts thereof.

The invention is also directed to medicaments or pharmaceutical compositions for treating diseases or disorders in which CGRP is involved, such as migraine, which comprise a compound of any of formulas (I) to (VI), or a pharmaceutically acceptable salt thereof, and a pharmaceutically acceptable carrier.

The invention is also directed to the use of a compound of any of formulas (I) to (VI) for treating diseases or disorders in which CGRP is involved, such as migraine.

The invention is further directed to a method for the manufacture of a medicament or a composition for treating diseases or disorders in which CGRP is involved, such as migraine, comprising combining a compound of any of formulas (I) to (VI) with one or more pharmaceutically acceptable carriers.

It is to be understood that where one or more of the above recited structures or substructures recite multiple substituents having the same designation each such variable may be the same or different from each similarly designated variable. For example, $R^a$ is recited multiple times in formula I, and each $R^a$ in formula I may independently be any of the substructures defined under $R^a$. The invention is not limited to structures and substructures wherein each $R^a$ must be the same for a given structure. The same is true with respect to any variable appearing multiple times in a structure or substructure.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

The present invention includes compounds of formula I wherein on or more hydrogen atoms are replaced by deuterium.

Tautomers of compounds defined in any of formulas (I) to (VI) are also included within the scope of the present invention. For example, compounds including carbonyl $-CH_2C(O)-$ groups (keto forms) may undergo tautomerism to form hydroxyl $-CH=C(OH)-$ groups (enol forms). Both keto and enol forms are included within the scope of the present invention.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As will be appreciated by those of skill in the art, even where substituents are disclosed which may form a ring structure (for instance $R^6$ may form a ring with $R^7$), not all combinations of substituents are susceptible to ring formation. Moreover, even those substituents capable of ring formation may or may not form a ring structure.

Also as appreciated by those of skill in the art, halo or halogen as used herein are intended to include chloro, fluoro, bromo and iodo.

As used herein, "alkyl" is intended to mean linear and branched structures having no carbon-to-carbon double or triple bonds. Thus $C_{1-6}$alkyl is defined to identify the group as having 1, 2, 3, 4, 5 or 6 carbons in a linear or branched arrangement, such that $C_{1-6}$alkyl specifically includes, but is not limited to, methyl, ethyl, n-propyl, iso-propyl, n-butyl, iso-butyl, tert-butyl, pentyl and hexyl. $C_0$ or $C_0$alkyl is defined to identify the presence of a direct covalent bond.

"Cycloalkyl" is an alkyl, part or all of which forms a ring of three or more atoms.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term "heterocycle" or "heterocyclic", as used herein except where noted, represents a stable 5- to 7-membered monocyclic- or stable 8- to 11-membered bicyclic heterocyclic ring system which is either saturated or unsaturated, and which consists of carbon atoms and from one to six heteroatoms selected from the group consisting of N, O, S, P and Si, and wherein the nitrogen, sulfur and phosphorus heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic groups include, but are not limited to, azetidine, chroman, dihydrofuran, dihydropyran, dioxane, dioxolane, hexahydroazepine, imidazolidine, imidazolidinone, imidazoline, imidazolinone, indoline, isochroman, isoindoline, isothiazoline, isothiazolidine, isoxazoline, isoxazolidine, morpholine, morpholinone, oxazoline, oxazolidine, oxazolidinone, oxetane, 2-oxohexahydroazepin, 2-oxopiperazine, 2-oxopiperidine, 2-oxopyrrolidine, piperazine, piperidine, pyran, pyrazolidine, pyrazoline, pyrrolidine, pyrroline, quinuclidine, tetrahydrofuran, tetrahydropyran, thiamorpholine, thiazoline, thiazolidine, thiomorpholine and N-oxides thereof.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to six heteroatoms selected from the group consisting of N, O, S, P and Si, and wherein the nitrogen, sulfur and phosphorus heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. Suitable salts derived from organic or inorganic acids include the hydrochloride, hydrobromide, nitrate, phosphate, sulfate, carbonate, acetate, fumarate, tartrate, citrate, malate, succinate, lactate, stearate, propionate, benzoate, hippurate, maleate, gluconate, mesylate, tosylate, cleat; lactobionate, laurylsulphate, ascorbate, adipate, gluceptate, glutamate, glucoronate, besylate, caprylate, isetionate, gentisate, malonate, napsylate, edisylate, pamoate, xinafoate, napadisylate, oxalate, cinnamate, mandelate, undecylenate and camsylate.

Free bases and salts derived from inorganic bases include aluminum, ammonium, dimethylammonium, ethanolammounium, calcium, copper, ferric, ferrous, lithium, magnesium, manganic salts, manganous, potassium, sodium, zinc, and the like. Other suitable salts derived from cations include organic amines, such as lysine, arginine, tromethamine, benzathine, benethamine, meglumine, choline, epolamine, hydrabamine, ethylenediamine and imidazole.

It will be understood that, as used herein, references to the compounds of Formula I are meant to also include the pharmaceutically acceptable salts.

The number of certain variables present in certain instances is defined in terms of the number of carbons present. For example, variable "p" is occasionally defined as follows: "p is 0 to 2q+1, for a substituent with q carbons". Where the substituent is "$(F)_pC_{1-3}$ alkyl" this means that when there is one carbon, there are up to 2(1)+1=3 fluorines. When there are two carbons, there are up to 2(2)+1=5 fluorines, and when there are three carbons there are up to 2(3)+1=7 fluorines.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

The subject compounds are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The ability of the compounds of the present invention to act as CGRP antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases; neurogenic cutaneous redness, skin rosaceousness and erythema; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of any of Formulas (I) to (VI) or the other drugs may have utility, where the combination of the drugs together are safer or more effective than either drug alone. Such other drug(s) may be administered, by a route and in an amount commonly used therefor, contemporaneously or sequentially with a compounds of any of Formulas (I) to (VI). When a compound of any of Formulas (I) to (VI) is used contemporaneously with one or more other drugs, a pharmaceutical composition in unit dosage form containing such other drugs and the compound of any of Formulas (I) to (VI) is preferred. However, the combination therapy may also include therapies in which the compound of any of Formulas (I) to (VI) and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of any of Formulas (I) to (VI).

For example, the present compounds may be used in conjunction with an anti-migraine agent, such as ergotamine and dihydroergotamine, or other serotonin agonists, especially a 5-$HT_{1B/1D}$ agonist, for example sumatriptan, naratriptan, zolmitriptan, eletriptan, almotriptan, frovatriptan, donitriptan, and rizatriptan, a 5-$HT_{1D}$ agonist such as PNU-142633 and a 5-$HT_{1F}$ agonist such as LY334370; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as ibuprofen, ketoprofen, fenoprofen, naproxen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or glucocorticoids. Similarly, the instant compounds may be administered with an analgesic such as aspirin, acetaminophen, phenacetin, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist, such as memantine; an NR2B antagonist; a bradykinin-1 receptor antagonist; an adenosine A1 receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; a renin inhibitor; a granzyme B inhibitor; a substance P antagonist; an endothelin antagonist; a norepinephrin precursor; anti-anxiety agents such as diazepam, alprazolam, chlordiazepoxide and chlorazepate; serotonin 5$HT_2$ receptor antagonists; opiod agonists such as codeine, hydrocodone, tramadol, dextropropoxyphene and febtanyl; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; an antidepressant, for example amitriptyline, nortriptyline, clomipramine, imipramine, venlafaxine, doxepin, protriptyline, desipramine, trimipramine, or imipramine; a leukotriene antagonist, for example montelukast or zafirlukast; an inhibitor of nitric oxide or an inhibitor of the synthesis of nitric oxide; histamine (H3) agonists; glutamergic modulators; orexin antagonists; and carbonic anhydrase inhibitors, such as acetazolamide.

Also, the present compounds may be used in conjunction with gap junction inhibitors; neuronal calcium channel blockers such as civamide; AMPA/KA antagonists such as LY293558; sigma receptor agonists; and vitamin B2.

Also, the present compounds may be used in conjunction with ergot alkaloids other than ergotamine and dihydroergotamine, for example ergonovine, ergonovine, methylergonovine, metergoline, ergoloid mesylates, dihydroergocornine, dihydroergocristine, dihydroergocryptine, dihydro-α-ergocryptine, dihydro-β-ergocryptine, ergotoxine, ergocornine, ergocristine, ergocryptine, α-ergocryptine, β-ergocryptine, ergosine, ergosine, bromocriptine, or methysergide.

Additionally, the present compounds may be used in conjunction with a beta-adrenergic antagonist such as timolol, propanolol, atenolol, metoprolol or nadolol, and the like; a MAO inhibitor, for example phenelzine; a calcium channel blocker, for example flunarizine, diltiazem, amlodipine, felodipine, nisolipine, isradipine, nimodipine, lomerizine, verapamil, nifedipine, or prochlorperazine; neuroleptics such as olanzapine, droperidol, prochlorperazine, chlorpromazine and quetiapine; an anticonvulsant such as topiramate, zonisamide, tonabersat, carabersat, levetiracetam, lamotrigine, tiagabine, gabapentin, pregabalin or divalproex sodium; an anti-hypertensive such as an angiotensin II antagonist, for example losartan, irbesartin, valsartan, eprosartan, telmisartan, olmesartan, medoxomil, candesartan and candesartan cilexetil, an angiotensin I antagonist, an angiotensin converting enzyme inhibitor such as lisinopril, enalapril, captopril, benazepril, quinapril, perindopril, ramipril and trandolapril; or botulinum toxin type A or B.

The present compounds may be used in conjunction with a potentiator such as caffeine, an H2-antagonist, simethicone, aluminum or magnesium hydroxide; a decongestant such as oxymetazoline, epinephrine, naphazoline, xylometazoline, propylhexedrine, or levo-desoxy-ephedrine; an antitussive such as caramiphen, carbetapentane, or dextromethorphan; a diuretic; a prokinetic agent such as metoclopramide or domperidone; a sedating or non-sedating antihistamine such as acrivastine, azatadine, bromodiphenhydramine, brompheniraminc, carbinoxamine, chlorpheniramine, clemastine, dexbrompheniramine, dexchlorpheniramine, diphenhydramine, doxylamine, loratadine, phenindamine, pheniramine, phenyltoloxamine, promethazine, pyrilamine, terfenadine, triprolidine, phenylephrine, phenylpropanolamine, or pseudoephedrine. The present compounds also may be used in conjunction with anti-emetics.

In a particularly preferred embodiment the present compounds are used in conjunction with an anti-migraine agent, such as: ergotamine or dihydroergotamine; a 5-$HT_1$ agonist, especially a 5-$HT_{1B/1D}$ agonist, in particular, sumatriptan, naratriptan, zolmitriptan, eletriptan, almotriptan, frovatriptan, donitriptan, avitriptan and rizatriptan, and other serotonin agonists; and a cyclooxygenase inhibitor, such as a selective cyclooxygenase-2 inhibitor, in particular, rofecoxib, etoricoxib, celecoxib, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may be provided in the form of tablets containing 1.0 to 1000 milligrams of the active ingredient, particularly about 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Reaction Schemes

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

Simple modifications of these routes, including different protecting group strategies, application of well-precedented methodology, and the use of starting materials and reagents other than those described in the foregoing schemes, may be used to provide other intermediates and claimed compounds.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reactions schemes may be varied to facilitate the reaction or to avoid unwanted reaction products.

SCHEME 1

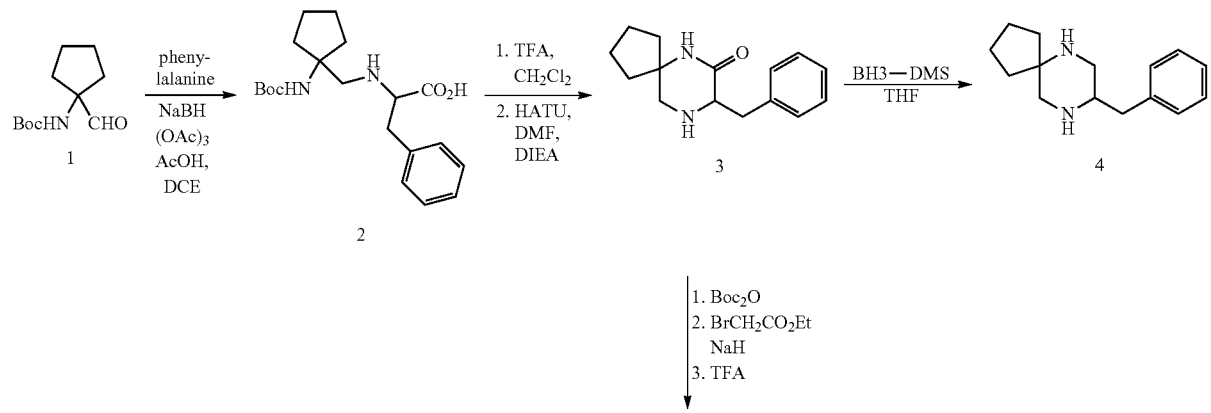

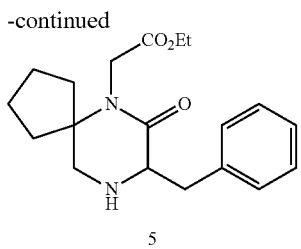

5

A representative synthesis of a substituted piperazinone intermediate is shown in Scheme 1. N-Boc-cycloleucinal (1) may be reductively aminated with phenylalanine to produce intermediate 2. Intermediate 2 may then be deprotected and cyclized to form piperazinone 3 using a variety of amide bond forming reagents, including HATU in DMF. Other reagents which might be useful for this transformation include EDC, BOP, and pyClu. Further transformations can be executed on 3, for example reduction of the amide carbonyl with borane to produce piperazine 4. Piperazinone 3 might also be protected and further functionalized by base catalyzed alkylation of the amide nitrogen, followed by deprotection to provide piperazinone 5. Those skilled in the art of organic synthesis will recognize that straightforward modifications of this methodology may be used to access other piperazinoneone intermediates. Additionally, use of alternative starting materials to 1 and phenylalanine may be used to provide different products.

SCHEME 2

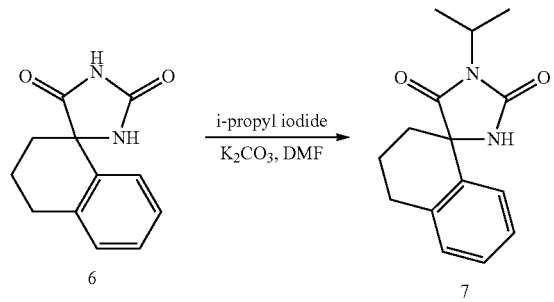

Examples of alternative heterocycles (but not limited to) are shown in Scheme 2. Readily available ketones and aldehydes may be converted to hydantoins under Bucherer-Bergs conditions, using ammonium carbonate and either sodium cyanide or potassium cyanide. Scheme 2 shows that the hydantoin 6 can be selectively alkylated at N-3 using potassium carbonate and 2-iodopropane, in DMF, to prepare 7.

A representative synthesis of a spiroazaoxindole intermediate is shown in Scheme 3. 7-Azaindole (8) may be protected with a variety of protecting groups, such as the 2-(trimethylsilyl)ethoxymethyl group shown in Scheme 3. Following the method of Marfat and Carter (Tetrahedron Lett., 1987, 28, 4027-4030), treatment of 9 with pyridine hydrobromide perbromide provides the dibromoazaoxindole 10, which may be reduced to the corresponding azaoxindole 11 by reaction with zinc. The key alkylation of 11 with 1,2-bis(bromomethyl)-4-nitrobenzene (12, Cava et al., *J. Org. Chem.* 2000, 65, 5413-5415) is carried out using cesium carbonate in DMF to afford the spiroazaoxindole 13. A variety of other bases and solvents may be employed in this alkylation reaction, and use of a different alkylating agent than the dibromide shown here can lead to other products. Reduction of the nitro compound 13, for example using hydrogenation over palladium, and a two-step deprotection affords the corresponding aniline 15. The methodology shown in Scheme 3 is not limited to azaoxindoles such as 11, but may be applied to a variety of suitably protected heterocyclic systems to give the corresponding spiro compounds.

SCHEME 3

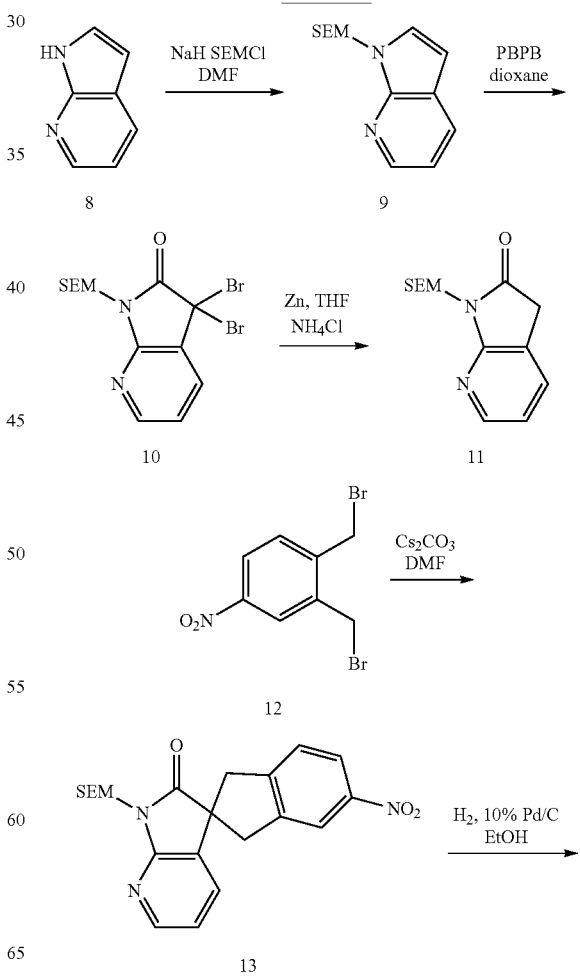

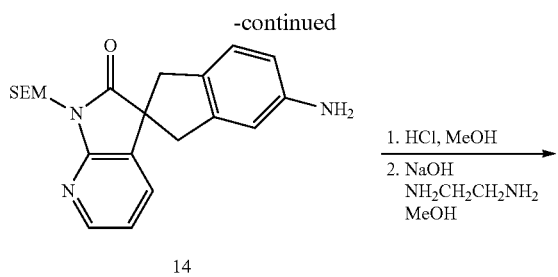

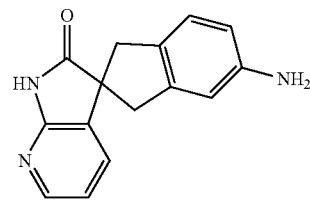

Spiroazaoxindole intermediates, such as those illustrated in Scheme 3, may be resolved to give pure enantiomers using techniques familiar to those skilled in the art. For example, chromatography of the protected intermediate 14 on a Chiral-Pak OD column can be used to provide the individual enantiomers (R)-14 and (S)-14, and these enantiomers may be converted to the corresponding anilines [(R)-15 and (S)-15] by the two-step deprotection. The methodology described herein may be applied to such enantiomerically pure aniline intermediates to give the individual enantiomers of the compounds of the present invention. Resolution may be effected by other methodologies, such as fractional crystallization of diastereomeric salts, and it may be carried out on other synthetic intermediates or on the final products. Alternatively, an asymmetric synthesis of a key intermediate could be used to provide an enantiomerically enriched final product.

Aniline intermediates, such as those described in Scheme 3, may be converted to a variety of other key intermediates that are useful in the synthesis of the compounds of the present invention. For example, Scheme 4 illustrates methodology for conversion of a representative aniline into several quinoline intermediates.

SCHEME 4

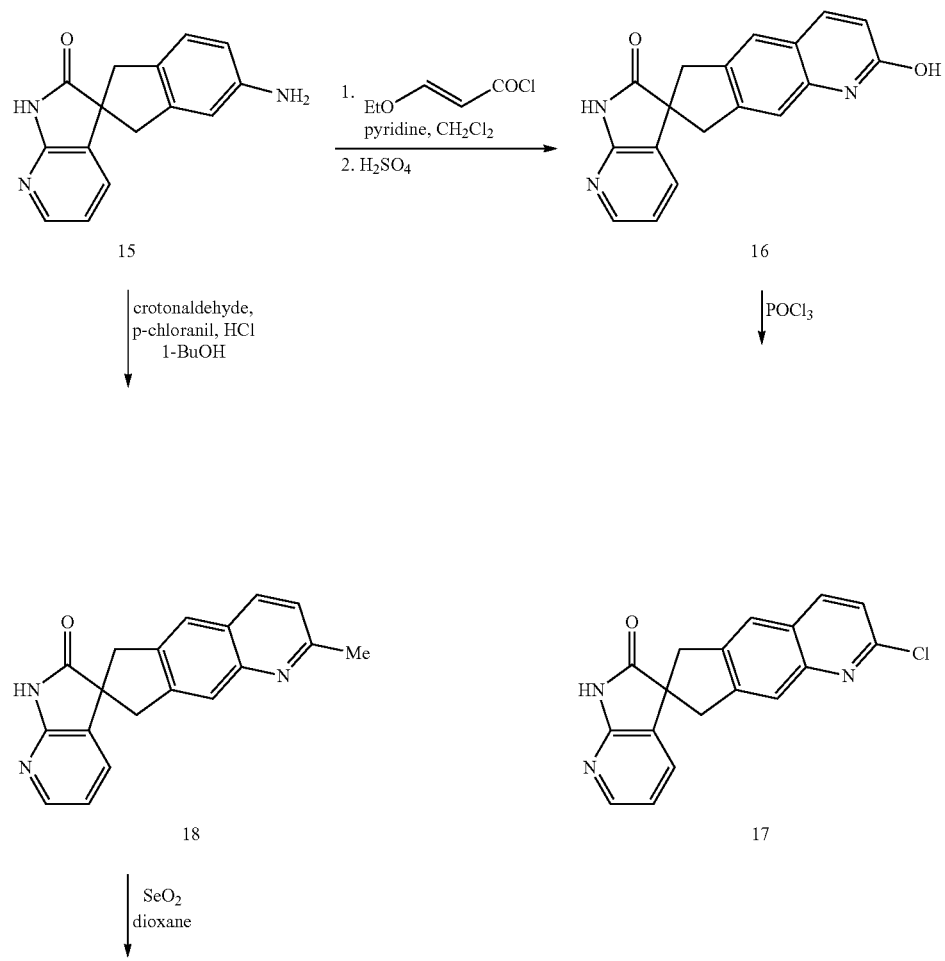

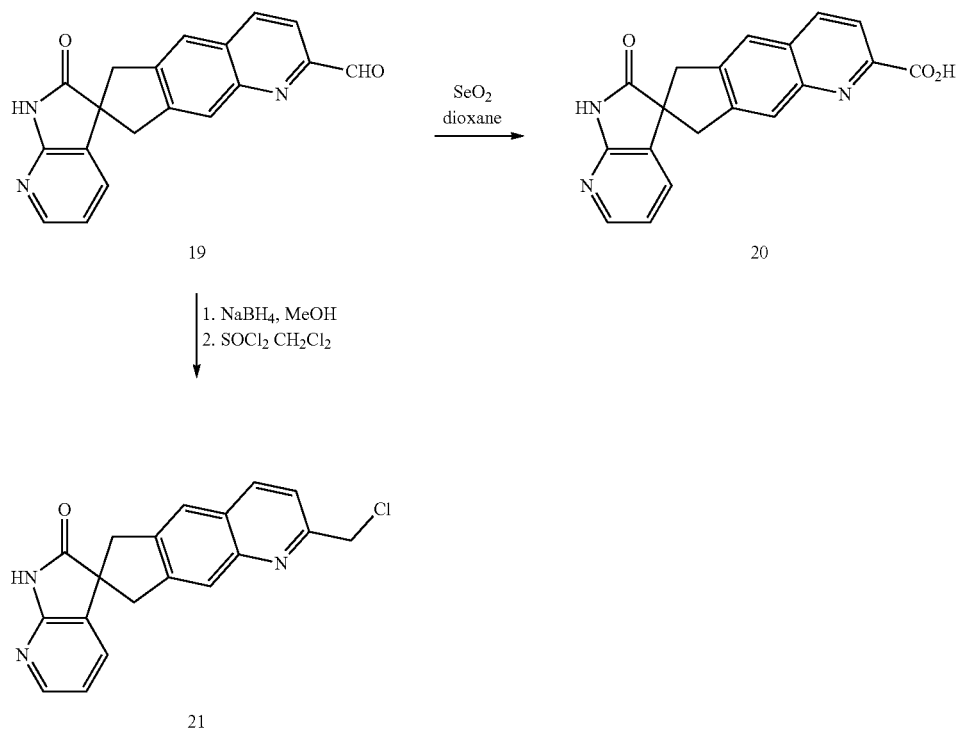

Aniline 15 may be acylated with (E)-3-ethoxyaeryloyl chloride and treatment of the resulting amide with sulfuric acid leads to hydroxyquinoline 16, which can be converted to the corresponding chloride 17 by heating in phosphorus oxychloride. Condensation of aniline 15 with crotonaldehyde in the presence of acid and an oxidant affords the 2-methylquinoline 18. The use of other aldehydes under similar conditions can lead to alternatively substituted quinolines. Oxidation of quinoline 18 with selenium dioxide can provide either aldehyde 19 or carboxylic acid 20, depending on the amount of oxidant used and the duration of the reaction. Reduction of aldehyde 19 with sodium borohydride provides the corresponding alcohol, and treatment of this with thionyl chloride may be used to give the chloride 21. Intermediates such as 17, 19, 20 and 21 may be converted to compounds of the present invention using a variety of known methodology. While the methodology shown in Scheme 4 is exemplified using aniline 15, it is understood that it may be applied to a variety of aniline substrates, such as those described herein, in order to provide various quinoline intermediates.

The methodology illustrated in the foregoing Schemes 34 describes the synthesis of some intermediates that are useful for making the compounds of the present invention. While the examples shown involve analogues of aniline 15, those skilled in the art will appreciate that such methodology may be extended to a variety of other anilines to give other useful intermediates. For example, Scheme 5 illustrates the synthesis of heterocyclic intermediates that are analogous to those in Scheme 4 but of a more general structure.

SCHEME 5

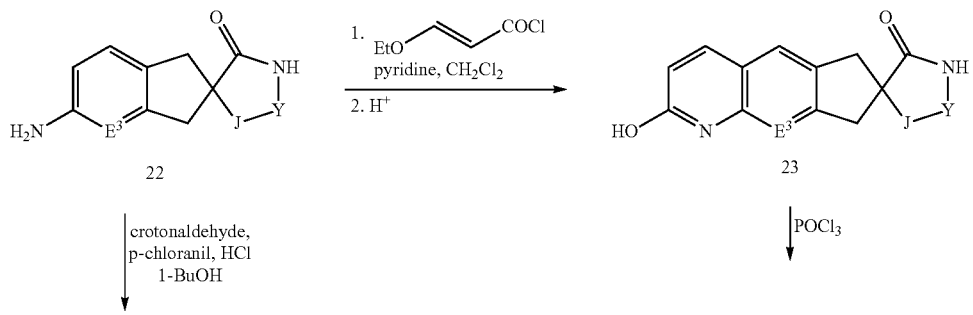

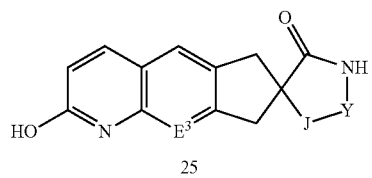

25

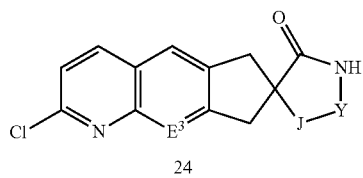

24

SeO₂
dioxane ↓

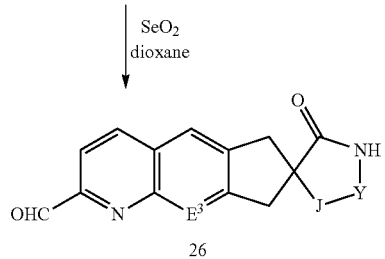

26

SeO₂
dioxane →

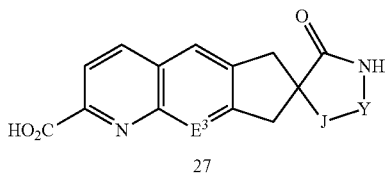

27

1. NaBH₄, MeOH
2. SOCl₂ CH₂Cl₂ ↓

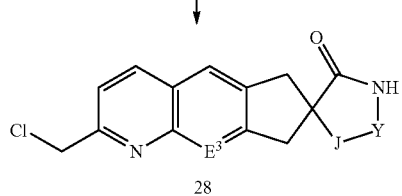

28

It is understood by those skilled in the art that in some cases alternative reagents or conditions may be used to effect the transformations in Scheme 5. In some cases, additional chemical steps may be required to obtain the compounds of interest, or various protecting group strategies may be employed.

The intermediates described in Schemes 4-5 may be used to synthesize the compounds of the present invention using a variety of known methodologies. Some of these methodologies are illustrated in Scheme 6. Standard reductive amination of an aldehyde like 26 with a suitable amine (RR'NH) may be used to obtain a final product of interest (29). Similarly, a standard coupling reaction may be used to convert carboxylic acid 27 to amide 30, which may be another example of the present invention when R and R' are selected appropriately.

SCHEME 6

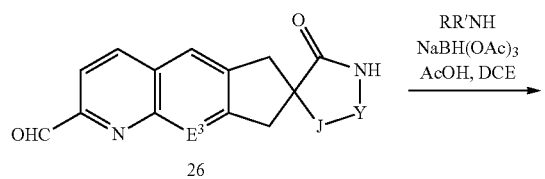

26

RR'NH
NaBH(OAc)₃
AcOH, DCE →

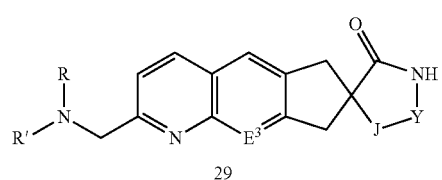

29

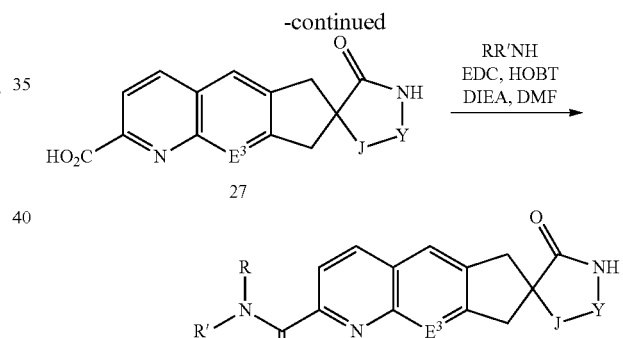

27

RR'NH
EDC, HOBT
DIEA, DMF →

30

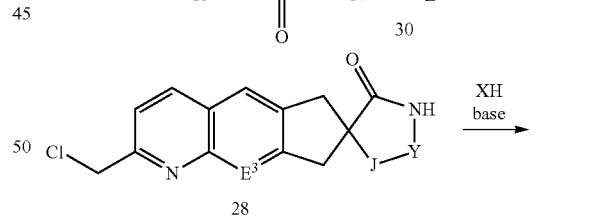

28

XH
base →

31

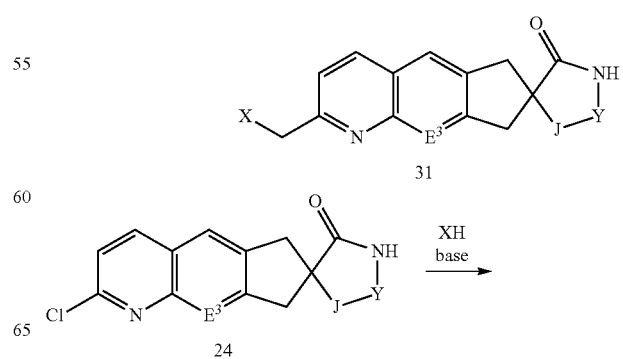

24

XH
base →

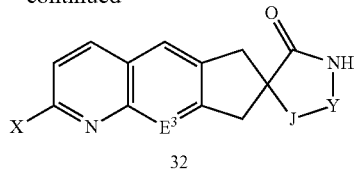

Scheme 6 also illustrates the coupling of chlorides 24 and 28 with a suitable partner (XH), usually under basic conditions, to give other compounds of the present invention (31 and 32). The precise nature of RR'NH or XH not only determines the identity of the final compound of interest, but also influences the choice of conditions under which the reaction is performed. For example, reductive amination of 26 may be performed using alternative conditions to those shown in Scheme 6, such as sodium cyanoborohydride in MeOH, depending on the exact natures of 26 and the amine. Similarly, the coupling of RR'NH and acid 27 may be carried out under a variety of known conditions, such as use of an alternative coupling reagent like PyBOP, or activation of the carboxylic acid as an acid anhydride or acid chloride. One skilled in the art will infer from precedent in the chemical literature, and from those examples given herein, suitable conditions for reaction of either 24 or 28 with XH, which is usually an amine, lactam or similar compound.

Simple modifications of these routes, including different protecting group strategies, application of well-precedented methodology, and the use of starting materials and reagents other than those described in the foregoing schemes, may be used to provide other acids of interest.

In some cases the final product may be further modified, for example, by manipulation of substituents. These manipulations may include, but are not limited to, reduction, oxidation, alkylation, acylation, and hydrolysis reactions which are commonly known to those skilled in the art.

The following examples are provided so that the invention might be more fully understood. These examples are illustrative only and should not be construed as limiting the invention in any way.

Intermediate 1

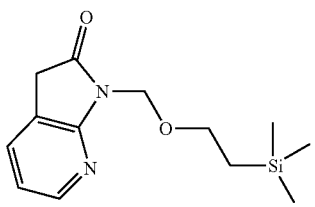 [SMILES: C[Si](C)(C)CCOCN1C(=O)Cc2cccnc21]

1-{[2-(Trimethylsilyl)ethoxy]methyl}-1,3-dihydro-2H-pyrrolo[2,3-b]pyridin-2-one

Step A. 1-{[2-Trimethylsilyl)ethoxy]methyl}-1H-pyrrolo[2,3-b]pyridine

Sodium hydride (60% dispersion in mineral oil, 16.2 g, 0.404 mol) was added in portions over 25 min to a solution of 7-azaindole (39.8 g, 0.337 mol) in DMF (200 mL) at 0° C. and the mixture was stirred for 1 h. 2-(Trimethylsilyl)ethoxymethyl chloride (71.8 mL, 0.404 mol) was then added slowly over 15 min, keeping the temperature of the reaction mixture below 10° C. After 1 h, the reaction was quenched with H$_2$O (500 mL) and the mixture was extracted with CH$_2$Cl$_2$ (5×300 mL). The combined organic layers were washed with brine, dried over MgSO$_4$, filtered, concentrated and dried under high vacuum to give the title compound. MS: m/z=249 (M+1).

Step B. 3,3-Dibromo-1-{[2-(trimethylsilyl)ethoxy]methyl}-1,3-dihydro-2H-pyrrolo[2,3-b]pyridin-2-one A solution of 1-{[2-(trimethylsilyl)ethoxy]methyl}-1H-pyrrolo[2,3-b]pyridine from Step A (43.1 g, 0.174 mol) in dioxane (300 mL) was added dropwise over 30 min to a suspension of pyridine hydrobromide perbromide (277 g, 0.868 mol) in dioxane (300 mL). The reaction was stirred at ambient temperature using an overhead mechanical stirrer. After 60 min, the biphasic reaction mixture was quenched with H$_2$O (300 mL) and extracted with EtOAc. The aqueous layer was washed with EtOAc (2×300 mL) and the combined organic layers were washed with H$_2$O (4×300 mL; the final wash was pH 5-6), then brine (300 mL), then dried over MgSO$_4$, filtered and concentrated under reduced pressure. The crude product was immediately dissolved in CH$_2$Cl$_2$ and the solution filtered through a plug of silica, eluting with CH$_2$Cl$_2$ until the dark red color had completely eluted from the plug. The filtrate was washed with saturated aqueous NaHCO$_3$ (400 mL), then brine (400 mL), dried over MgSO$_4$ and concentrated in vacuo to give the title compound. MS: m/z=423 (M+1).

Step C. 1-{[2-(Trimethylsilyl)ethoxy]methyl}-1,3-dihydro-2H-pyrrolo[2,3-b]pyridin-2-one Zinc (100 g, 1.54 mol) was added to a solution of 3,3-dibromo-1-{[2-(trimethylsilyl)ethoxy]methyl}-1,3-dihydro-2H-pyrrolo[2,3-b]pyridin-2-one from Step B (65 g, 0.154 mol) in THF (880 mL) and saturated aqueous ammonium chloride (220 mL). After 3 h, the reaction was filtered and concentrated in vacuo. The residue was partitioned between EtOAc and H$_2$O which resulted in the formation of a white precipitate. Both layers were filtered through a Celite pad and the layers were separated. The aqueous layer was washed with EtOAc (2×) and the combined organic layers were washed with H$_2$O, dried over MgSO$_4$, filtered, and concentrated. The crude product was filtered through a plug of silica gel eluting with EtOAc:CH$_2$Cl$_2$-1:9 and the eluant was concentrated under reduced pressure to provide the title compound. MS: m/z=265 (M+1).

Intermediate 2

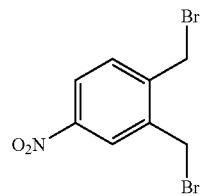 [SMILES: O=[N+]([O-])c1ccc(CBr)c(CBr)c1]

1,2-Bis bromomethyl)-4-nitrobenzene

Step A. (4-Nitro-1,2-phenylene)dimethanol

4-Nitrophthalic acid (40 g, 189.5 mmol) in tetrahydrofuran (500 mL) was added dropwise over 1.5 h to a solution of borane-THF complex (1 M, 490 mL, 490 mmol), keeping the reaction temperature between 0° C. and 5° C. After the addition, the reaction was allowed to warm slowly to ambient temperature and stirred for 18 h. Methanol (100 mL) was added carefully and the precipitated solid dissolved. The mixture was concentrated in vacuo to about 500 mL, cooled to 0° C., and 10 N sodium hydroxide was added to adjust the pH to 10-11. This mixture was extracted with EtOAc (3×600 mL) and the combined organic layers were washed with brine, dried over $Na_2SO_4$, filtered, and concentrated in vacuo to give the title compound. MS: m/z=207 (M-OH+$CH_3$CN).

Step B. 1,2-Bis(bromomethyl)-4-nitrobenzene

Phosphorus tribromide (3.9 mL, 41.1 mmol) in ether (50 mL) was added dropwise over 1.5 h to a solution of (4-nitro-1,2-phenylene)dimethanol from Step A (6.85 g, 37.4 mmol) in ether (150 mL). After 18 h, the reaction mixture was cooled to 0° C. and quenched with $H_2O$ (25 mL). The layers were separated and the organic layer was washed with $H_2O$, then saturated aqueous $NaHCO_3$, dried over $Na_2SO_4$, filtered, and concentrated in vacuo to give the title compound. MS: m/z=309 (M+1).

Intermediate 3

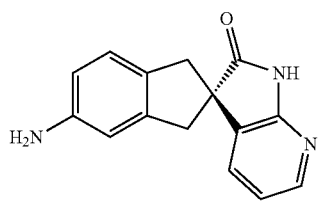 [SMILES: Nc1ccc2c(c1)C[C@]1(C2)C(=O)Nc2ncccc21]

(S)-5-Amino-1,3-dihydrospiro[indene-2,3'-pyrrolo[2,3-b]pyridin]-2'(1'H)-one

Step A. (±)-5-Nitro-1'-{[2-(trimethylsilyl)ethoxy]methyl}-1,3-dihydrospiro[indene-2,3'-pyrrolo[2,3-b]pyridin]-2'(1'H)-one To a solution of 1,2-bis(bromomethyl)-4-nitrobenzene (40.9 g, 132 mmol, described in Intermediate 2) and 1-{[2-(trimethylsilyl)ethoxy]methyl}-1,3-dihydro-2H-pyrrolo[2,3-b]pyridin-2-one (31.5 g, 119 mmol, described in Intermediate 1) in DMF (2 L) was added cesium carbonate (129 g, 397 mmol), portionwise, over 5 min. After 18 h, acetic acid (7.6 mL) was added and the mixture was concentrated to a volume of about 500 mL, then partitioned between EtOAc (1.5 L) and $H_2O$ (1 L). The organic layer was washed with $H_2O$ (1 L), then brine (500 mL), then dried over $Na_2SO_4$, filtered, and concentrated in vacuo. The crude product was purified by silica gel chromatography, eluting with a gradient of hexane:EtOAc—100:0 to 0:100, to give the title compound. MS: m/z=412 (M+1).

Step B. (S)-5-Amino-1'-{[2-(trimethylsilyl)ethoxy]methyl}-1,3-dihydrospiro[indene-2,3'-pyrrolo[2,3-b]pyridin]-2'(1'H)-one A mixture of 10% Pd/C (3 g) and (±)-5-nitro-1'-{[2-(trimethylsilyl)ethoxy]methyl}-1,3-dihydrospiro[indene-2,3'-pyrrolo[2,3-b]pyridin]-2'(1'H)-one from Step A (19.1 g, 46.4 mmol) was stirred vigorously in EtOH (400 mL) under an atmosphere of hydrogen (ca. 1 atm). After 18 h, the mixture was filtered through a pad of Celite, washing extensively with MeOH, and the filtrate was concentrated in vacuo to give the crude racemic compound. The enantiomers were resolved by HPLC, utilizing a Chiralcel OD column and eluting with MeOH. The first major peak to elute was (S)-5-amino-1'-{[2-(trimethylsilyl)ethoxy]methyl}-1,3-dihydrospiro[indene-2,3'-pyrrolo[2,3-b]pyridin]-2'(1'H)-one, the title compound, and the second major peak to elute was (R)-5-amino-1'-{[2-(trimethylsilyl)ethoxy]methyl}-1,3-dihydrospiro[indene-2,3'-pyrrolo[2,3-b]pyridin]-2'(1'H)-one. MS: m/z=382 (M+1).

Step C. (S)-5-Amino-1,3-dihydrospiro[indene-2,3'-pyrrolo[2,3-b]pyridin]-2'(1'H)-one A solution of (S)-5-amino-1'-{[2-(trimethylsilyl)ethoxy]methyl}-1,3-dihydrospiro[indene-2,3'-pyrrolo[2,3-b]pyridin]-2'(1'H)-one from Step B (13.7 g, 35.9 mmol) in methanol (300 mL) was saturated with HCl (g). The mixture was resaturated with HCl (g) every 30 min until the starting material was consumed, and then concentrated in vacuo. The residue was dissolved in MeOH (150 mL) and treated with ethylenediamine (2.4 mL, 35.9 mmol) and 10 N sodium hydroxide (7.2 mL, 72 mmol) to adjust the mixture to pH 10. After 30 min, the mixture was diluted with $H_2O$ (400 mL) and extracted with $CHCl_3$ (2×1 L). The combined organic layers were dried over $Na_2SO_4$, filtered, and concentrated in vacuo. The crude material was triturated with MeOH (50 mL) to give the title compound. MS: m/z=252 (M+1).

Intermediate 4

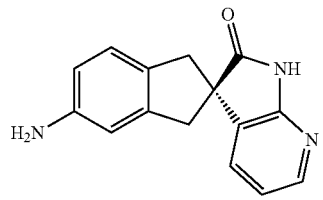 [SMILES: Nc1ccc2c(c1)C[C@@]1(C2)C(=O)Nc2ncccc21]

(R)-5-Amino-1,3-dihydrospiro[indene-2,3'-pyrrolo[2,3-b]pyridin]-2'(1'H)-one

Essentially following the procedures described for Intermediate 3, but using (R)-5-amino-1'-{[2-(trimethylsilyl)ethoxy]methyl}-1,3-dihydrospiro[indene-2,3'-pyrrolo[2,3-b]pyridin]-2'(1'H)-one in Step C, the title compound was obtained. MS: m/z=252 (M+1).

Intermediate 5

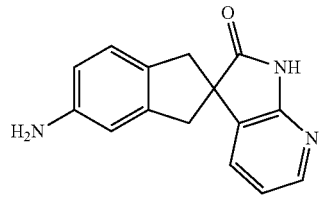 [SMILES: Nc1ccc2c(c1)CC1(C2)C(=O)Nc2ncccc21]

(±)-5-Amino-1,3-dihydrospiro[indene-2,3'-pyrrolo[2,3-b]pyridin]-2'(1'H)-one

Essentially following the procedures described for Intermediate 3, but without the chiral HPLC resolution of (±)-5-amino-1'-{[2-(trimethylsilyl)ethoxy]methyl}-1,3-dihydrospiro[indene-2,3'-pyrrolo[2,3-b]pyridin]-2'(1'H)-one, the title compound was obtained. MS: m/z=252 (M+1).

Intermediate 6

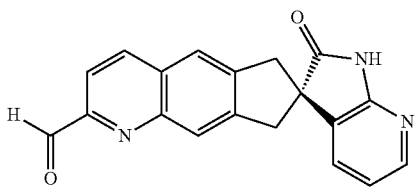 [SMILES: O=Cc1ccc2cc3c(cc2n1)C[C@]1(C3)C(=O)Nc2ncccc21]

(S)-2'-Oxo-1',2',6,8-tetrahydrospiro[cyclopenta[g]quinoline-7,3'-pyrrolo[2,3-b]pyridine]-2-carbaldehyde Step A. (S)-2-Methyl-6,8-dihydrospiro[cyclopenta[g]quinoline-7,3'-pyrrolo[2,3-b]pyridin]-2'(1'H)-one (S)-5-Amino-1,3-dihydrospiro[indene-2,3'-pyrrolo[2,3-b]pyridin]-2'(1'H)-one (6.10 g, 24.3 mmol, described in Intermediate 3) and p-chloranil (5.97 g, 24.3 mmol) were suspended in a mixture of 1-BuOH (6 mL) and conc. hydrochloric acid (6 mL, 73 mmol) and the mixture was heated to reflux. Crotonaldehyde (2.04 g, 29.1 mmol) in 1-BuOH (4 mL) was added dropwise over 20 min. After a further 20 min at reflux, the mixture was allowed to cool to ambient temperature and 10 N NaOH (7.3 mL, 73 mmol) was added and the neutralized mixture was concentrated in vacuo to give a brown residue. The crude product was purified by silica gel chromatography, eluting with a gradient of CH₂Cl₂:MeOH:NH₄OH—100:0:0 to 95:4.5:0.5, to give the title compound. MS: m/z=302 (M+1).

Step B. (S)-2'-Oxo-1',2',6,8-tetrahydrospiro[cyclopenta[g]quinoline-7,3'-pyrrolo[2,3-b]pyridine]-2-carbaldehyde A mixture of (S)-2-methyl-6,8-dihydrospiro[cyclopenta[g]quinoline-7,3'-pyrrolo[2,3-b]pyridin]-2'(1'H)-one from Step A (1.30 g, 4.31 mmol) and selenium dioxide (718 mg, 6.47 mmol) in dioxane (50 mL) and H₂O (5 mL) was heated at reflux for 4 h. The reaction mixture was concentrated to dryness under reduced pressure. The residue was purified by silica gel chromatography, eluting with a gradient of CH₂Cl₂:MeOH—100:0 to 90:10. Product-containing fractions were combined, toluene was added, and the mixture was concentrated in vacuo to give the title compound. MS: m/z=316 (M+1).

Intermediate 7

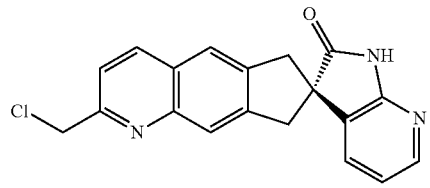 [SMILES: O=C1Nc2ncccc2[C@@]12Cc1cc3ccc(CCl)nc3cc1C2]

(S)-2-(Chloromethyl)-6,8-dihydrospiro[cyclopenta[g]quinoline-7,3'-pyrrolo[2,3-b]pyridin]-2'(1'H)-one Step A. (S)-2-(Hydroxymethyl)-6,8-dihydrospiro[cyclopenta[g]quinoline-7,3'-pyrrolo[2,3-b]pyridin]-2'(1'H)-one To a stirred suspension of (S)-2'-oxo-1',2',6,8-tetrahydrospiro[cyclopenta[g]quinoline-7,3'-pyrrolo[2,3-b]pyridine]-2-carbaldehyde (80 mg, 025 mmol, described in Intermediate 6) in a mixture of MeOH (5 mL) and DMSO (1 mL) was added sodium borohydride (19 mg, 0.51 mmol). The resulting mixture was stirred at ambient temperature for 1 h, then the MeOH was removed in vacuo. The residue was partitioned between saturated aqueous NaHCO₃ (20 mL) and CH₂Cl₂ (20 mL). The aqueous layer was extracted further with CH₂Cl₂ (2×20 mL). The combined organic extracts were dried over Na₂—SO₄, filtered, and concentrated in vacuo to give the title compound in sufficient purity for use in the next step. MS: m/z=318 (M+1).

Step B. (S)-2-(Chloromethyl)-6,8-dihydrospiro[cyclopenta[g]quinoline-7,3'-pyrrolo[2,3-b]pyridin]-2'(1'H)-one To a stirred solution of (S)-2'-(hydroxymethyl)-6,8-dihydrospiro[cyclopenta[g]quinoline-7,3'-pyrrolo[2,3-b]pyridin]-2'(1'H)-one from Step A (203 mg, 0.64 mmol) in CH₂Cl₂ (20 mL) was added thionyl chloride (761 mg, 6.40 mmol) and the resulting mixture was stirred at ambient temperature for 1 h, then concentrated in vacuo. The residue was partitioned between saturated aqueous NaHCO₃ (20 mL) and CH₂Cl₂ (30 mL). The aqueous layer was extracted further with CH₂Cl₂ (2×30 mL). The combined organic extracts were dried over Na₂SO₄, filtered, and concentrated in vacuo to give the title compound in sufficient purity for use in the next step. MS: m/z=336 (M+1).

Intermediate 8

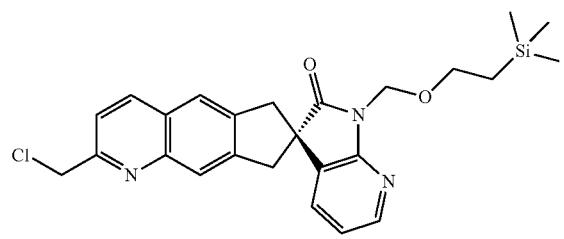 [SMILES: C[Si](C)(C)CCOCN1C(=O)[C@]2(Cc3cc4ccc(CCl)nc4cc3C2)c2cccnc21]

(S)-2-(Chloromethyl)-1'-{[2-(trimethylsilyl)ethoxy]methyl}-6,8-dihydrospiro[cyclopenta[g]quinoline-7,3'-pyrrolo[2,3-b]pyridin]-2'(1'H)-one Step A. (S)-2-(Hydroxymethyl)-1'-{[2-(trimethylsilyl)ethoxy]methyl}-6,8-dihydrospiro[cyclopenta[g]quinoline-7,3'-pyrrolo[2,3-b]pyridin]-2'(1'H)-one To a stirred solution of (S)-2-(hydroxymethyl)-6,8-dihydrospiro[cyclopenta[g]quinoline-7,3'-pyrrolo[2,3-b]pyridin]-2'(1'H)-one (1.67 g, 5.26 mmol, described in Intermediate 7) in DMF (10 mL) at 0° C. was added sodium hydride (60% dispersion in mineral oil; 210 mg, 5.26 mmol) and the mixture was stirred for 30 min. 2-(Trimethylsilyl)ethoxymethyl chloride (0.93 mL, 5.26 mmol) was then added dropwise. After 90 min, the reaction was quenched with saturated aqueous NaHCO$_3$ (50 mL) and the mixture was extracted with CH$_2$Cl$_2$ (3×100 mL). The combined organic layers were washed with brine, dried over Na$_2$SO$_4$, filtered, concentrated in vacuo. The crude product was purified by silica gel chromatography, eluting with a gradient of CH$_2$Cl$_2$:MeOH:NH$_4$OH—100:0:0 to 90:9:1, to give the title compound. MS: m/z=448 (M+1).

Step B. (S)-2-(Chloromethyl)-1'-{[2-(trimethylsilyl)ethoxy]methyl}-6,8-dihydrospiro[cyclopenta[g]quinoline-7,3'-pyrrolo[2,3-b]pyridin]-2'(1'H)-one To a stirred solution of (S)-2-(hydroxymethyl)-1'-{[2-(trimethylsilyl)ethoxy]methyl}-6,8-dihydrospiro[cyclopenta[g]quinoline-7,3'-pyrrolo[2,3-b]pyridin]-2'(1'H)-one from Step A (1.44 g, 3.22 mmol) in CH$_2$Cl$_2$ (10 mL) was added thionyl chloride (7.66 g, 64.3 mmol) and the resulting mixture was stirred at ambient temperature for 30 min, then concentrated in vacuo. The residue was concentrated in vacuo from toluene (2×10 mL) to give the title compound in sufficient purity for use in the next step. MS: m/z=466 (M+1).

Intermediate 9

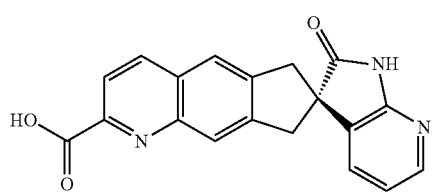 [SMILES: O=C(O)c1ccc2cc3c(cc2n1)C[C@]1(C3)C(=O)Nc2ncccc21]

(S)-2'-Oxo-1',2',6,8-tetrahydrospiro[cyclopenta[g]quinoline-7,3'-pyrrolo[2,3-b]pyridine]-2-carboxylic acid Step A. (S)-2'-Oxo-1',2',6,8-tetrahydrospiro[cyclopenta[g]quinoline-7,3'-pyrrolo[2,3-b]pyridine]-2-carboxylic acid A mixture of (S)-2-methyl-6,8-dihydrospiro[cyclopenta[g]quinoline-7,3'-pyrrolo[2,3-b]pyridin]-2'(1'H)-one (500 mg, 1.66 mmol, described in Intermediate 6) and selenium dioxide (552 mg, 4.97 mmol) in dioxane (30 mL) and H$_2$O (3 mL) was heated at reflux for 18 h. The reaction mixture was allowed to cool, then it was filtered through a pad of Celite, and the filtrate was concentrated in vacuo to give the title compound. MS: m/z=332 (M+1).

Intermediate 10

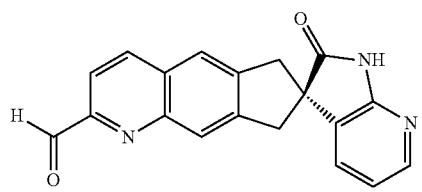 [SMILES: O=Cc1ccc2cc3c(cc2n1)C[C@@]1(C3)C(=O)Nc2ncccc21]

(R)-2'-Oxo-1',2',6,8-tetrahydrospiro[cyclopenta[g]quinoline-7,3'-pyrrolo[2,3-b]pyridine]-2-carbaldehyde Essentially following the procedures described for Intermediate 6, but using (R)-5-amino-1,3-dihydrospiro[indene-2,3'-pyrrolo[2,3-b]pyridin]-2'(1'H)-one (described in Intermediate 4) in place of (S)-5-amino-1,3-dihydrospiro[indene-2,3'-pyrrolo[2,3-b]pyridin]-2'(1'H)-one, the title compound was obtained. MS: m/z=316 (M+1).

Intermediate 11

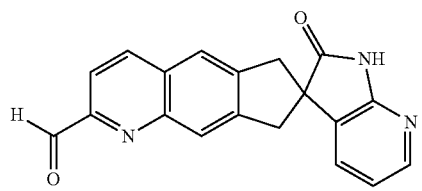 [SMILES: O=Cc1ccc2cc3c(cc2n1)CC1(C3)C(=O)Nc2ncccc21]

(±)-2'-Oxo-1',2',6,8-tetrahydrospiro[cyclopenta[g]quinoline-7,3'-pyrrolo[2,3-b]pyridine]-2-carbaldehyde Essentially following the procedures described for Intermediate 6, but using (±)-5-amino-1,3-dihydrospiro[indene-2,3'-pyrrolo[2,3-b]pyridin]-2'(1'H)-one (described in Intermediate 5) in place of (S)-5-amino-1,3-dihydrospiro[indene-2,3'-pyrrolo[2,3-b]pyridin]-2'(1'H)-one, the title compound was obtained. MS: m/z=316 (M+1).

Intermediate 12

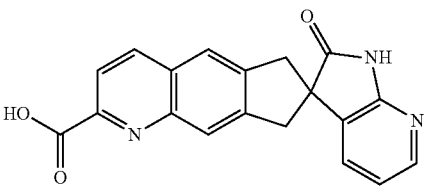 [SMILES: O=C(O)c1ccc2cc3c(cc2n1)CC1(C3)C(=O)Nc2ncccc21]

(±)-2'-oxo-1',2',6,8-tetrahydrospiro[cyclopenta[g] quinoline-7,3'-pyrrolo[2,3-b]pyridine]-2-carboxylic acid Essentially following the procedures described for Intermediate 9, but using (±)-2-methyl-6,8-dihydrospiro[cyclopenta[g]quinoline-7,3'-pyrrolo[2,3-b]pyridin]-2'(1'H)-one (described in Intermediate 11) in place of (S)-2-methyl-6,8-dihydrospiro[cyclopenta[g]quinoline-7,3'-pyrrolo[2,3-b]pyridin]-2'(1'H)-one, the title compound was obtained. MS: m/z=332 (M+1).

Intermediate 13

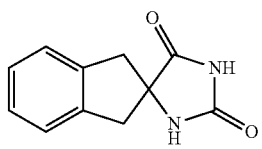 [SMILES: O=C1NC(=O)C2(Cc3ccccc3C2)N1]

(±)Spiro[imidazolidine-4,2'-indane]-2,5-dione

Step A. (±)-Spiro[imidazolidine-4,2'-indane]-2,5-dione

A stirred mixture of 2-indanone (10 g, 22.6 mmol), sodium cyanide (3.3 g, 67.3 mmol), and ammonium carbonate (22 g, 228 mol) in H$_2$O (50 mL) and EtOH (50 mL) was heated to 70° C. for 3 h, then allowed to cool to ambient temperature. The precipitate was collected by filtration and washed with H$_2$O (5×100 mL). Drying in vacuo afforded the title compound. MS: m/z=202 (M+1).

Intermediate 14

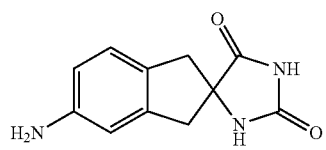 [SMILES: Nc1ccc2c(c1)CC1(C2)NC(=O)NC1=O]

(±)-5'-Amino-spiro[imidazolidine-4,2'-indane]-2,5-dione

Step A. (±)-5'-Nitro-spiro[imidazolidine-4,2'-indane]-2,5-dione

A solution of (±)-spiro[imidazolidine-4,2'-indane]-2,5-dione (3.0 g, 14.8 mmol, described in Intermediate 13) in conc. nitric acid (33 mL) was stirred at ambient temperature for 1 h. The reaction was then poured onto crushed ice and the resultant solid was isolated by filtration. The crude material was recrystallized from ethanol to give the title compound. MS: m/z=248 (M+1).

Step B. (±)-5'-Amino-spiro[imidazolidine-4,2'-indane]-2,5-dione

To a suspension of (±)-5'-nitro-spiro[imidazolidine-4,2'-indane]-2,5-dione (1.77 g, 7.16 mmol) in EtOAc (100 mL) and MeOH (100 mL) was added 10% Pd/C (400 mg) and the reaction stirred vigorously under hydrogen (ca. 1 atm). After 1 h, the catalyst was filtered off and the filtrate was concentrated to yield the title compound. MS: m/z=218 (M+1).

Intermediate 15

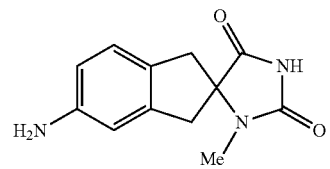 [SMILES: CN1C(=O)NC(=O)C12Cc1ccc(N)cc1C2]

(±)-5'-Amino-3-methyl-spiro[imidazolidine-4,2'-indane]-2,5-dione

Step A. 2-(Methylamino)indane-2-carbonitrile hydrochloride

To a mixture of 2-indanone (20.0 g, 151 mmol) in MeOH (20 mL) was added methylamine hydrochloride (10.2 g, 151 mmol). To the stirred mixture was added H$_2$O (20 mL) and a fine homogenous slurry developed. The reaction mixture was cooled to 0° C. and KCN (9.84 g, 151 mmol) in H$_2$O (20 mL) was added slowly over 30 min, such that the temperature did not exceed 10° C., then stirring was continued at ambient temperature for 18 h. The reaction mixture was extracted with Et$_2$O (250 mL) and the organic extract was washed with brine (50 mL) then dried over MgSO$_4$. HCl (g) was bubbled through the vigorously stirred solution for 10 minutes and a white solid precipitated. The solid was filtered, washed with Et$_2$O, and dried to yield the title compound. MS: m/z=173 (M+1).

Step B. (±)-3-Methyl-spiro[imidazolidine-4,2'-indane]-2,5-dione

To a stirred mixture of 2-(methylamino)indane-2-carbonitrile hydrochloride from Step A (6.0 g, 28.8 mmol) in AcOH (45 mL) was added a solution of potassium cyanate (4.65 g, 57 mmol) in H$_2$O (6 mL) and the reaction mixture was stirred for 1 h. The mixture was poured into cold H$_2$O (150 mL) and the precipitate was isolated by filtration, washed with H$_2$O and air dried. The crude solid was suspended in 1 N HCl (30 mL) and stirred to 50° C. for 2 h. The reaction mixture was cooled, filtered, and the isolated solid washed with H$_2$O and dried in vacuo to yield the title compound. MS: m/z=217 (M+1).

Step C. (±)-3-Methyl-5'-nitro-spiro[imidazolidine-4,2'-indane]-2,5-dione

To stirred fuming (90%) nitric acid (100 mL) was slowly added (±)-3-methyl-spiro[imidazolidine-4,2'-indane]-2,5-dione (4.5 g, 20.9 mmol) in portions over 30 min. The reaction mixture was diluted with H$_2$O (200 mL) and the precipitate was collected by filtration, washed with H$_2$O and dried in vacuo to give the title compound. MS: m/z=262 (M+1).

(±)-5'-Amino-3-methyl-spiro[imidazolidine-4,2'-indane]-2,5-dione

Essentially following the procedures described for Intermediate 14, but using (±)-3-methyl-5'-nitro-spiro[imidazolidine-4,2'-indane]-2,5-dione in place of (±)-5'-nitro-spiro[imidazolidine-4,2'-indane]-2,5-dione, the title compound was prepared. MS: m/z=232 (M+1).

Intermediate 16

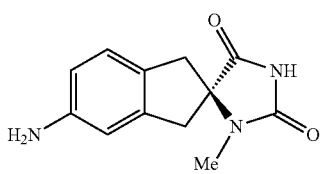 [SMILES: CN1C(=O)NC(=O)[C@]12Cc1ccc(N)cc1C2]

(R)-5'-Amino-3-methyl-spiro[imidazolidine-4,2'-indane]-2,5-dione

Step A. (R)-3-Methyl-5'-nitro-spiro[imidazolidine-4,2'-indane]-2,5-dione (±)-3-Methyl-5'-nitro-spiro[imidazolidine-4,2'-indane]-2,5-dione (described in Intermediate 15) was dissolved in a mixture of MeOH, CH₃CN and diethylamine and the enantiomers were resolved by HPLC, utilizing a ChiralPak AD column and eluting with CH₃CN:MeOH—90:10. The first major peak to elute was (S)-3-methyl-5'-nitro-spiro[imidazolidine-4,2'-indane]-2,5-dione and the second major peak to elute was (R)-3-methyl-5'-nitro-spiro[imidazolidine-4,2'-indane]-2,5-dione, the title compound. MS: m/z 262 (M+1).

(R)-5'-Amino-3-methyl-spiro[imidazolidine-4,2'-indane]-2,5-dione

Essentially following the procedures described for Intermediate 14, but using (R)-3-methyl-5'-nitro-spiro[imidazolidine-4,2'-indane]-2,5-dione in place of (±)-5'-nitro-spiro[imidazolidine-4,2'-indane]-2,5-dione, the title compound was prepared. MS: m/z=232 (M+1).

Intermediate 17

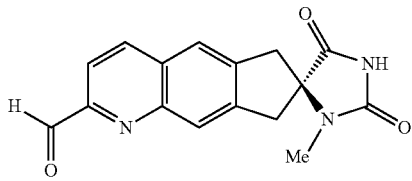 [SMILES: CN1C(=O)NC(=O)[C@]12Cc1cc3ccc(C=O)nc3cc1C2]

(7R)-3'-Methyl-2,5'-dioxo-6,8-dihydrospiro[cyclopenta[g]quinoline-7,4'-imidazolidine]-2-carbaldehyde Step A. (7R)-2,3'-Dimethyl-6,8-dihydro-2'H,5'H-spiro[cyclopenta[g]quinoline-7,4'-imidazolidine]-2',5'-dione (R)-5'-Amino-3-methyl-spiro[imidazolidine-4,2'-indane]-2,5-dione (3.00 g, 13.0 mmol, described in Intermediate 16) and p-chloranil (3.19 g, 13.0 mmol) were suspended in a mixture of 1-BuOH (3.2 mL) and conc. hydrochloric acid (3.2 mL, 39 mmol) and the mixture was heated to reflux. Crotonaldehyde (1.09 g, 15.6 mmol) in 1-BuOH (3 mL) was added dropwise over 20 min. After a further 20 min at reflux, the mixture was allowed to cool to ambient temperature and 10 N NaOH (3.9 mL, 39 mmol) was added and the neutralized mixture was concentrated in vacuo to give a brown residue. The crude product was purified by silica gel chromatography, eluting with a gradient of CH₂Cl₂:MeOH—100:0 to 90:10, to give the title compound. MS: m/z=282 (M+1).

Step B. (7R)-3'-Methyl-2',5'-dioxo-6,8-dihydrospiro[cyclopenta[g]quinoline-7,4'-imidazolidine]-2-carbaldehyde A mixture of (7R)-2,3'-dimethyl-6,8-dihydro-2'H,5'H-spiro[cyclopenta[g]quinoline-7,4'-imidazolidine]-2',5'-dione from Step A (1.70 g, 6.04 mmol), selenium dioxide (1.01 g, 9.06 mmol) and powdered molecular sieves, 4 Å, (680 mg) in dioxane (60 mL) was heated at reflux for 90 min. The reaction mixture was filtered through a pad of Celite, washing with CH₂Cl₂-MeOH, and the filtrate was concentrated under reduced pressure. The residue was partitioned between saturated aqueous NaHCO₃ (400 mL) and EtOAc (1.5 L) containing MeOH (30 mL). The organic layer was extracted and the aqueous layer was washed with EtOAc (400 mL). The combined organic layers were washed with brine, dried over Na₂SO₄, filtered, and concentrated in vacuo to give the title compound. MS: m/z=296 (M+1).

Intermediate 18

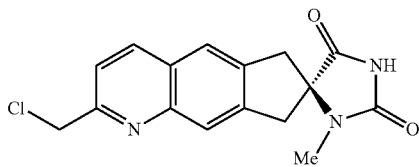 [SMILES: CN1C(=O)NC(=O)[C@]12Cc1cc3ccc(CCl)nc3cc1C2]

(7R)-2-(Chloromethyl)-3'-methyl-6,8-dihydro-2'H,5'H-spiro[cyclopenta[g]quinoline-7,4'-imidazolidine]-2',5'-dione Step A. (7R)-2-(Hydroxymethyl)-3'-methyl-6,8-dihydro-2'H,5'H-spiro[cyclopenta[g]quinoline-7,4'-imidazolidine]-2',5'-dione To a stirred solution of (7R)-3'-methyl-2',5'-dioxo-6,8-dihydrospiro[cyclopenta[g]quinoline-7,4'-imidazolidine]-2-carbaldehyde (2.62 g, 8.89 mmol, described in Intermediate 17) in MeOH (20 mL) was added NaBH₄ (672 mg, 17.8 mmol) and the mixture was stirred at ambient temperature for 1 h, then concentrated to dryness in vacuo. The crude product was purified by silica gel chromatography, eluting with a gradient of CH₂Cl₂:MeOH:NH₄OH—100:0:0 to 90:9:1, to give the title compound. MS: m/z=298 (M+1).

Step B. (7R)-2-(Chloromethyl)-3'-methyl-6,8-dihydro-2'H,5'H-spiro[cyclopenta[g]quinoline 7,4'-imidazolidine]-2',5'-dione To a stirred solution of (7R)-2-(hydroxymethyl)-3'-methyl-6,8-dihydro-2'H,5'H-spiro[cyclopenta[g]quinoline-7,4'-imidazolidine]-2',5'-dione from Step A (200 mg, 0.67 mmol)

in CH$_2$Cl$_2$ (5 mL) was added thionyl chloride (0.98 mL, 13.5 mmol) dropwise. The reaction mixture was stirred for 30 min and the precipitate was isolated by filtration. The filtrate was poured into saturated aqueous NaHCO$_3$ (20 mL) and this mixture was extracted with CH$_2$Cl$_2$ (3×30 mL). The combined organic extracts were dried over Na$_2$SO$_4$, filtered, and concentrated in vacuo to give a solid, which was combined with the filtered solid to give the title compound, which was of sufficient purity for use in subsequent steps. MS: m/z=316 (M+1).

Intermediate 19

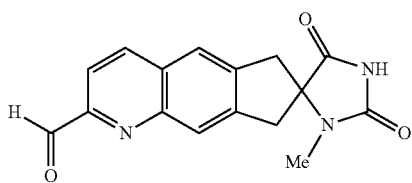 [SMILES: CN1C(=O)NC(=O)C12Cc1cc3ccc(C=O)nc3cc1C2]

(±)-3'-Methyl-2',5'-dioxo-6,8-dihydrospiro[cyclopenta[g]quinoline-7,4'-imidazolidine]-2-carbaldehyde Essentially following the procedures described for Intermediate 17, but using (±)-5'-amino-3-methyl-spiro[imidazolidine-4,2'-indane]-2,5-dione (described in Intermediate 15) in place of (R)-5'-amino-3-methyl-spiro[imidazolidine-4,2'-indane]-2,5-dione, the title compound is prepared. MS: m/z=296 (M+1).

Intermediate 20

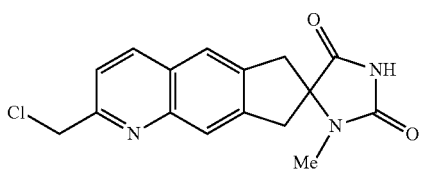 [SMILES: CN1C(=O)NC(=O)C12Cc1cc3ccc(CCl)nc3cc1C2]

(±)-2-(Chloromethyl)-3'-methyl-6,8-dihydro-2'H, 5'H-spiro[cyclopenta[g]quinoline-7,4'-imidazolidine]-2',5'-dione Essentially following the procedures described for Intermediate 18, but using (±)-3'-methyl-2',5'-dioxo-6,8-dihydrospiro[cyclopenta[g]quinoline-7,4'-imidazolidine]-2-carbaldehyde (described in Intermediate 19) in place of (7R)-3'-methyl-2',5'-dioxo-6,8-dihydrospiro[cyclopenta[g] quinoline-7,4'-imidazolidine]-2-carbaldehyde, the title compound is prepared. MS: m/z=316 (M+1).

Intermediate 21

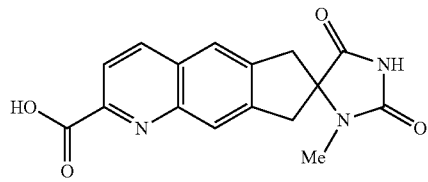 [SMILES: CN1C(=O)NC(=O)C12Cc1cc3ccc(C(=O)O)nc3cc1C2]

(±)-3'-Methyl-2',5'-dioxo-6,8-dihydrospiro[cyclopenta[g]quinoline-7,4'-imidazolidine]-2-carboxylic acid A mixture of (±)-2,3'-dimethyl-6,8-dihydro-2'H,5'H-spiro[cyclopenta[g]quinoline-7,4'-imidazolidine]-2',5'-dione (500 mg, 1.78 mmol, described in Intermediate 19) and selenium dioxide (592 mg, 5.33 mmol) in dioxane (30 mL) and H$_2$O (3 mL) are heated at reflux for 18 h. The reaction mixture is allowed to cool, filtered through a pad of Celite, and the filtrate is concentrated in vacuo to give the title compound. MS: m/z=312 (M+1).

Intermediate 22

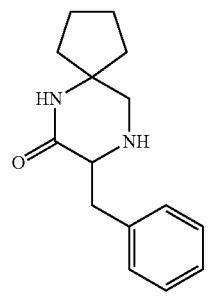 [SMILES: O=C1NC2(CCCC2)CNC1Cc1ccccc1]

(±)-8-Benzyl-6,9-diazaspiro[4.5]decan-7-one

Step A. (±)-N-({1-[(tert-Butoxycarbonyl)amino]cyclopentyl}methyl)phenylalanine

To a stirred solution of N-(tert-butoxycarbonyl)cycloleucinal (500 mg, 2.34 mmol) and DL-phenylalanine (1.16 g, 7.03 mmol) in AcOH (10 mL) was added Na(OAc)$_3$BH (596 mg, 2.81 mmol). The reaction mixture was stirred for 16 h and then filtered. The filtrate was purified by HPLC using a reversed phase C18 column and eluting with a gradient of H$_2$O:CH$_3$CN:CF$_3$CO$_2$H—90:10:0.1 to 5:95:0.1. The pure, product-containing fractions were combined and concentrated to give the title compound as the trifluoroacetate salt. MS: m/z=363 (M+1).

Step B. (±)-N-[(1-Aminocyclopentyl)methyl]phenylalanine

A solution of (±)-N-({1-[(tert-butoxycarbonyl)amino]cyclopentyl}methyl)phenylalanine from Step A (611 mg, 1.69 mmol) in CH$_2$Cl$_2$ (10 mL) and TFA (3 mL) was stirred for 16 h. The reaction mixture was concentrated in vacuo to give the title compound as the trifluoroacetate salt, which was of sufficient purity for use in subsequent steps. MS: m/z=263 (M+1).

Step C. (±)-8-Benzyl-6,9-diazaspiro[4.5]decan-7-one

A solution of (±)-N-[(1-aminocyclopentyl)methyl]phenylalanine from Step B (446 mg, 1.69 mmol), HATU (641 mg, 1.69 mmol), HOBT (7 mg, 0.045 mmol), and N-methylmorpholine (0.927 mL, 8.43 mmol) was stirred in DMF (1 mL) at ambient temperature for 1 h. The reaction mixture was purified directly by HPLC using a reversed phase C18 column and eluting with a gradient of $H_2O:CH_3CN:CF_3CO_2H$—90:10:0.1 to 5:95:0.1. The pure, product-containing fractions were combined and concentrated to give the title compound as the trifluoroacetate salt. MS: m/z=245 (M+1).

Intermediates 23-46

Essentially following the procedures outlined for Intermediate 22 the compounds listed in Table 1 were prepared. The requisite starting materials were commercially available, described in the literature, synthesized according to methodology described herein (vide supra), or readily synthesized by one skilled in the art of organic synthesis.

TABLE 1

| Intermediate | Structure | MS (M + 1) |
|---|---|---|
| 23 | 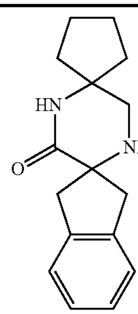 | 258 |
| 24 | 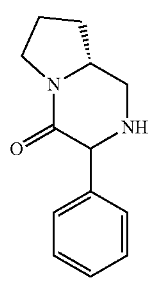 [SMILES: O=C1C(c2ccccc2)NC[C@H]2CCCN12] | 217 |
| 25 | 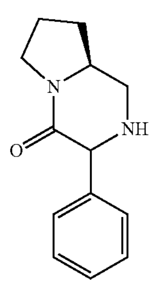 [SMILES: O=C1C(c2ccccc2)NC[C@@H]2CCCN12] | 217 |

TABLE 1-continued

| Intermediate | Structure | MS (M + 1) |
|---|---|---|
| 26 | 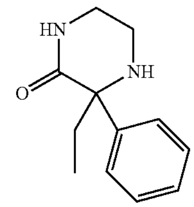 | 205 |
| 27 | 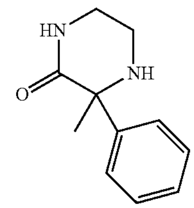 | 191 |
| 28 | 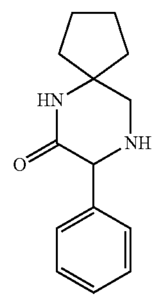 [SMILES: O=C1NC2(CCCC2)CNC1c1ccccc1] | 232 |
| 29 | 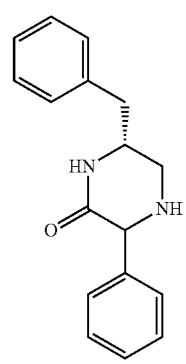 [SMILES: O=C1N[C@H](Cc2ccccc2)CNC1c1ccccc1] | 267 |
| 30 | 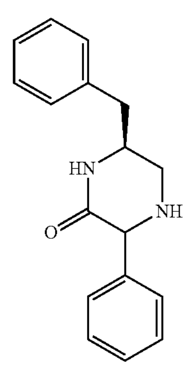 [SMILES: O=C1N[C@@H](Cc2ccccc2)CNC1c1ccccc1] | 267 |

TABLE 1-continued

| Intermediate | Structure | MS (M + 1) |
|---|---|---|
| 31 | 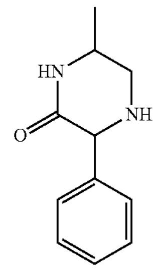 | 191 |
| 32 | 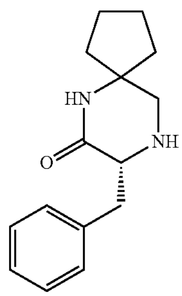 [SMILES: O=C1NC2(CCCC2)CN[C@@H]1Cc1ccccc1] | 245 |
| 33 | 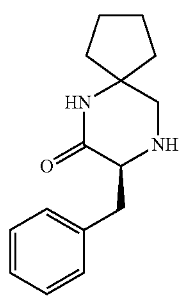 [SMILES: O=C1NC2(CCCC2)CN[C@H]1Cc1ccccc1] | 245 |
| 34 | 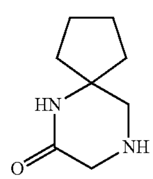 [SMILES: O=C1CNCC2(CCCC2)N1] | 155 |
| 35 | 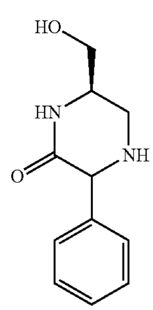 [SMILES: O=C1N[C@@H](CO)CNC1c1ccccc1] | 207 |
| 36 | | 259 |
| 37 | | 259 |
| 38 | | 273 |
| 39 | | 259 |
| 40 | | 218 |

TABLE 1-continued

| Intermediate | Structure | MS (M + 1) |
|---|---|---|
| 41 | 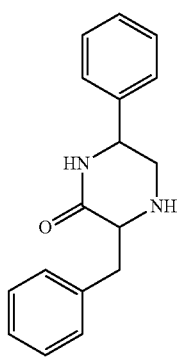 | 218 |
| 42 | 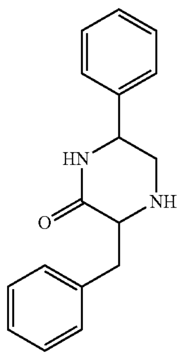 [SMILES: O=C1NC(c2ccccc2)CNC1Cc1ccccc1] | 267 |
| 43 | 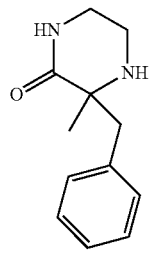 | 205 |
| 44 | 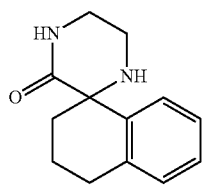 [SMILES: O=C1NCCNC12CCCc1ccccc12] | 217 |
| 45 | 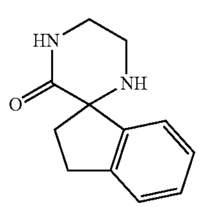 [SMILES: O=C1NCCNC12CCc1ccccc12] | 204 |

TABLE 1-continued

| Intermediate | Structure | MS (M + 1) |
|---|---|---|
| 46 | 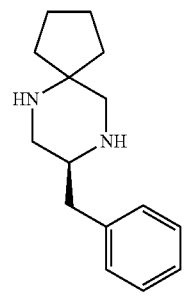 [SMILES: c1ccc(C[C@H]2CNC3(CCCC3)CN2)cc1] | 267 |

Intermediate 47

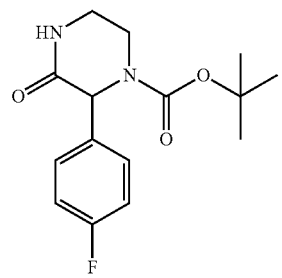 [SMILES: CC(C)(C)OC(=O)N1CCNC(=O)C1c1ccc(F)cc1]

(8S)-8-Benzyl-6,9-diazaspiro[4.5]decane

To a stirred solution of (8S)-8-benzyl-6,9-diazaspiro[4.5]decan-7-one (100 mg, 0.409 mmol, describe in Intermediate 33) in THF (10 mL) was added borane-methyl sulfide complex (1.23 mL, 2.46 mmol, 2M solution in THF). The reaction mixture was heated at 50° C. for 27 h, with additional borane-methyl sulfide complex (1.23 mL, 2.46 mmol, 2M solution in THF) added at 22 h. The reaction was quenched by slow the addition of 10% HCl (0.5 mL) and stirred for 16 h. The reaction was diluted with CH$_3$CN/MeOH (1 mL) and was purified by HPLC using a reversed phase C18 column and eluting with a gradient of H$_2$O:CH$_3$CN:CF$_3$CO$_2$H—90:10:0.1 to 5:95:0.1. The pure, product-containing fractions were combined and concentrated to give the title compound as the trifluoroacetate salt. MS: m/z=231 (M+1).

Intermediate 48

(±)-tert-Butyl 2-(4-fluorophenyl)-3-oxopiperazine-1-carboxylate

A solution of 3-(4-fluorophenyl)piperazin-2-one (996 mg, 5.13 mmol), Boc$_2$O (1.34 g, 6.15 mmol), and TEA (1.07 mL, 7.69 mmol) in CH$_2$Cl$_2$ (10 mL) was stirred for 72 h at ambient temperature. The reaction mixture was poured onto 1N NaOH (20 mL) and extracted with CH$_2$Cl$_2$ (3×20 mL). The combined organic layers were dried over Na$_2$SO$_4$, filtered, concentrated in vacuo. The crude product was purified by silica gel chromatography, eluting with a gradient of CH$_2$Cl$_2$: EtOAc—98:2 to 0:100, to give the title compound. MS: m/z=239 (M—C$_4$H$_9$).

Intermediate 49

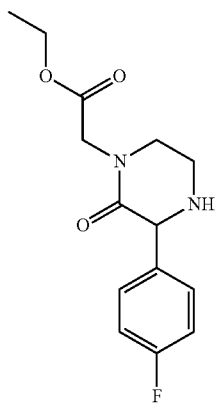 [SMILES: CCOC(=O)CN1CCNC(c2ccc(F)cc2)C1=O]

(±)-Ethyl[3-(4-fluorophenyl)-2-oxopiperazin-1-yl]acetate

Step A. (±)-tert-Butyl 4-(2-ethoxy-2-oxoethyl)-2-(4-fluorophenyl)-3-oxopiperazine-1-carboxylate A solution of (±)-tert-butyl 2-(4-fluorophenyl)-3-oxopiperazine-1-carboxylate (50.0 mg, 0.170 mmol, described in Intermediate 48) and sodium hydride (8.15 mg, 0.204 mmol, 60% dispersion in mineral oil) in DMF (1 mL) was stirred at ambient temperature for 0.5 h. Ethyl bromoacetate (0.023 mL, 0.204 mmol) was added and stirring continued for 16 h. The reaction mixture was purified by HPLC using a reversed phase C18 column and eluting with a gradient of H$_2$O: CH$_3$CN:CF$_3$CO$_2$H—90:10:0.1 to 5:95:0.1. The pure, product-containing fractions were neutralized with saturated aqueous NaHCO$_3$ (10 mL) and extracted with CH$_2$Cl$_2$ (3×10 mL). The combined organic layers were dried over Na$_2$SO$_4$, filtered, and concentrated in vacuo to give the title compound. MS: m/z=381 (M+1).

Step B. (±)-Ethyl[3-(4-fluorophenyl)-2-oxopiperazin-1-yl]acetate

A solution of (±)-tert-butyl 4-(2-ethoxy-2-oxoethyl)-2-(4-fluorophenyl)-3-oxopiperazine-1-carboxylate from Step A (55.0 mg, 0.145 mmol) in CH$_2$Cl$_2$ (2 mL) and TFA (1 mL) was stirred for 2 h. The reaction mixture was concentrated in vacuo to give the title compound as the trifluoroacetate salt, which was of sufficient purity for use in subsequent steps. MS: m/z=281 (M+1).

Intermediate 50

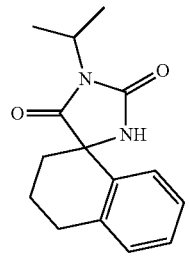 [SMILES: CC(C)N1C(=O)NC2(CCCc3ccccc32)C1=O]

(±)-1-Isopropyl-3',4'-dihydro-2H,2'H,5H-spiro[imidazolidine-4,1'-naphthalene]-2,5-dione To a stirred solution of (±)-3',4'-dihydro-2H,2'H,5H-spiro[imidazolidine-4,1'-naphthalene]-2,5-dione (150 mg, 0.694 mmol) in DMF (2 mL) was added potassium carbonate (144 mg, 1.04 mmol) and 2-iodopropane (0.083 mL, 0.832 mmol). The reaction was stirred at ambient temperature for 18 h and then partitioned between EtOAc (100 mL) and H$_2$O (100 mL). The layers were separated and the aqueous phase was extracted further with EtOAc (2×100 mL). The combined organic extracts were washed with brine (100 mL), dried over MgSO$_4$, filtered and concentrated under reduced pressure. The crude product was purified by silica gel chromatography, eluting with a gradient of hexane:EtOAc—75:25 to 50:50, to give the title compound. MS: m/z=259 (M+1).

Intermediate 51

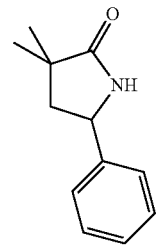

(±)-3,3-Dimethyl-5-phenylpyrrolidin-2-one

Step A. Methyl 2,2-dimethyl-4-oxo-4-phenylbutanoate

To a stirred mixture of 2,2-dimethyl-4-oxo-4-phenylbutanoic acid (1.1 g, 5.3 mmol) and potassium carbonate (0.88 g, 6.4 mmol) in DMSO (6.4 mL) was added methyl iodide (0.68 g, 4.80 mmol). The resulting mixture was stirred at ambient temperature for 15 h. The reaction mixture was diluted with water (100 mL) and diethyl ether (100 mL). The organic layer was then washed successively with water, saturated sodium bicarbonate, 1 M HCl, water and finally saturated brine. The organic layer was dried over Na$_2$SO$_4$, filtered, and concentrated in vacuo to provide the title compound which was subsequently used without further purification. MS: m/z=221 (M+1).

Step B. Ethyl 4-[(tert-butylsulfinyl)amino]-2,2-dimethyl-4-phenylbutanoate

To a stirred solution of methyl 2,2-dimethyl-4-oxo-4-phenylbutanoate from Step A (0.51 g, 2.3 mmol) and 2-methylpropane-2-sulfinamide (0.34 g, 2.8 mmol) in THF (12 mL) was added titanium tetraethoxide (1.4 g, 5.6 mmol). This mixture was then heated to 60° C. for 3 days. After cooling to 0° C. in an ice bath, sodium borohydride (0.18 g, 4.7 mmol) was added. Following 90 minutes of stirring at 0° C., MeOH was added slowly (drop-wise) until hydrogen gas evolution ceased. Next, saturated brine (~12 mL) was added, with vigorous stirring. The resulting mixture was filtered through celite using copious amounts of EtOAc. This organic filtrate was washed with saturated brine, dried over sodium sulfate, filtered and concentrated in vacuo. The crude product was purified by silica gel chromatography, eluting with a gradient of EtOAc:Hexane—10:90 to 70:30, to give the title compound. MS: m/z=340 (M+1).

Step C. (±)-3,3-Dimethyl-5-phenylpyrrolidin-2-one-one

To a stirred solution of Ethyl 4-[(tert-butylsulfinyl)amino]-2,2-dimethyl-4-phenylbutanoate from Step B (0.19 g, 0.55 mmol) in MeOH (10 mL) was added anhydrous HCl (gas, bubbled in for about 1 minute). After 20 minutes, nitrogen was bubbled though the reaction mixture for about 20 minutes. The initial solvent was removed in vacuo, and then more MeOH was added and removed in vacuo. The residue was then dissolved in MeOH (20 mL) and treated with triethylamine (0.22 g, 2.2 mmol). The solvent was once again removed in vacuo. This residue was then treated with toluene (10 mL) and triethylamine (0.22 g, 2.2 mmol) before being heated to 100° C. for 15 hours. After cooling to ambient temperature the solvent was removed in vacuo and the residue was partitioned between diethyl ether (50 mL) and 1 M HCl (50 mL). The organics were then successively washed with another volume of 1 M HCl, water and lastly saturated brine. The organic layer was dried over Na$_2$SO$_4$, filtered, and concentrated in vacuo to give the title compound which was used without further purification. MS: m/z=190 (M+1).

Example 1

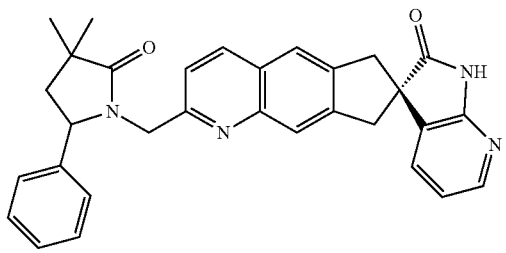 [SMILES: CC1(C)CC(c2ccccc2)N(Cc2ccc3cc4c(cc3n2)C[C@]2(C4)C(=O)Nc3ncccc32)C1=O]

(7S)-2-[(3,3-dimethyl-2-oxo-5-phenylpyrrolidin-1-yl)methyl]-6,8-dihydrospiro[cyclopenta[g]quinoline-7,3'-pyrrolo[2,3-b]pyridin]-2'(1'H)-one To a solution of (±)-3,3-dimethyl-5-phenylpyrrolidin-2-one (221 mg, 0.893 mmol, described in Intermediate 51) in DMF (0.5 mL), at ambient temperature, was added sodium hydride (60% dispersion in mineral oil; 37 mg, 0.923 mmol). The resulting mixture was stirred for 30 min, then (S)-2-(chloromethyl)-6,8-dihydrospiro[cyclopenta[g]quinoline-7, 3'-pyrrolo[2,3-b]pyridin]-2'(1'H)-one (100 mg, 0.298 mmol, described in Intermediate 7) was added and the resulting mixture was stirred at ambient temperature for 2 h. The reaction mixture was quenched with H$_2$O (0.1 mL) and purified directly by silica gel chromatography, eluting with a gradient of CH$_2$Cl$_2$:MeOH—100:0 to 95:5, to give the title compound. MS: m/z=547 (M+1). HRMS: m/z=547.2466; calculated m/z=547.2452 for C$_{32}$H$_{31}$N$_6$O$_3$.

Example 2

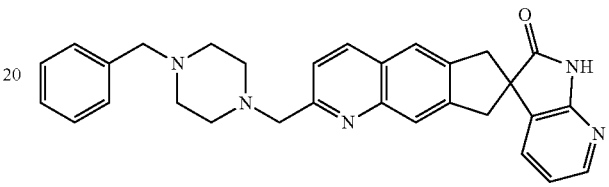

(±)-2-[(4-Benzylpiperazin-1-yl)methyl]-6,8-dihydrospiro[cyclopenta[g]quinoline-7,3'-pyrrolo[2,3-b] pyridin]-2'(1'H)-one To a stirred solution of (±)-2'-oxo-1',2',6,8-tetrahydrospiro [cyclopenta[g]quinoline-7,3'-pyrrolo[2,3-b]pyridine]-2-carbaldehyde (15 mg, 0.048 mmol, described in Intermediate 11), N-benzylpiperazine (13 mg, 0.071 mmol), and AcOH (0.014 mL, 0.24 mmol) in DCE (1 mL) was added sodium triacetoxyborohydride (15 mg, 0.072 mmol). The mixture was stirred for 2 h, quenched with TFA and concentrated to dryness in vacuo. The residue was dissolved in DMSO (1 mL) and purified by HPLC using a reversed phase C18 column and eluting with a gradient of H$_2$O:CH$_3$CN:CF$_3$CO$_2$H—90:10: 0.1 to 5:95:0.1. The pure, product-containing fractions were combined and concentrated to give the title compound as the trifluoroacetate salt. MS: m/z=476 (M+1). HRMS: m/z=476.2454; calculated m/z=476.2445 for C$_{30}$H$_{29}$N$_5$O.

Example 3

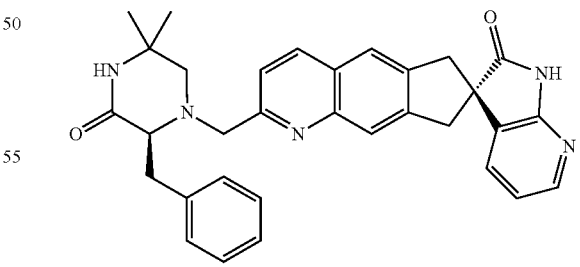

(7S)-2-{[(2S)-2-Benzyl-5,5-dimethyl-3-oxopiperazin-1-yl]methyl}-6,8-dihydrospiro[cyclopenta[g] quinoline-7,3'-pyrrolo[2,3-b]pyridin]-2'(1'H)-one To a stirred solution of (S)-2'-oxo-1',2',6,8-tetrahydrospiro [cyclopenta[g]quinoline-7,3'-pyrrolo[2,3-b]pyridine]-2-carbaldehyde (289 mg, 0.916 mmol, described in Intermediate 6), (3S)-3-benzyl-6,6-dimethylpiperazin-2-one (200 mg, 0.916 mmol, described in intermediate 41), and AcOH (0.262 mL, 4.58 mmol) in DCE (2 mL) was added sodium triacetoxyborohydride (233 mg, 1.09 mmol). The mixture was quenched with TFA and concentrated to dryness in vacuo. The residue was purified by HPLC using a reversed phase C18 column and eluting with a gradient of $H_2O:CH_3CN:CF_3CO_2H$—90:10:0.1 to 5:95:0.1. The pure, product-containing fractions were combined and concentrated to give the title compound as the trifluoroacetate salt. MS: m/z=518 (M+1). HRMS: m/z=518.2557; calculated m/z=518.2551 for $C_{32}H_{32}N_5O_2$.

Example 4

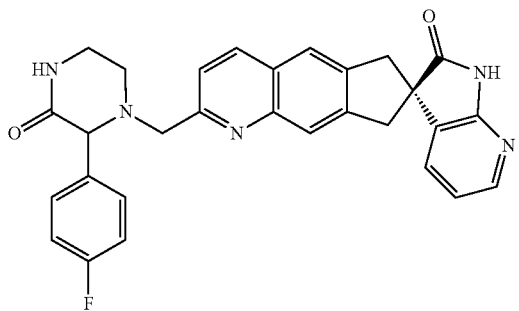 [SMILES: O=C1NCCN(Cc2ccc3cc4c(cc3n2)C[C@@]2(C4)C(=O)Nc3ncccc32)C1c1ccc(F)cc1]

(7R)-2-{[2-(4-Fluorophenyl)-3-oxopiperazin-1-yl]methyl}-6,8-dihydrospiro[cyclopenta[g]quinoline-7,3'-pyrrolo[2,3-b]pyridin]-2'(1'H)-one To a stirred solution of (R)-2'-oxo-1',2',6,8-tetrahydrospiro[cyclopenta[g]quinoline-7,3'-pyrrolo[2,3-b]pyridine]-2-carbaldehyde (20 mg, 0.063 mmol, described in Intermediate 10), (±)-3-(4-fluorophenyl)piperazin-2-one (15 mg, 0.076 mmol), and AcOH (0.018 mL, 0.317 mmol) in DCE (0.3 mL) was added sodium triacetoxyborohydride (20 mg, 0.095 mmol). The mixture was quenched with TFA and concentrated to dryness in vacuo. The residue was dissolved in DMSO (1 mL) and purified by HPLC using a reversed phase C18 column and eluting with a gradient of $H_2O:CH_3CN:CF_3CO_2H$—90:10:0.1 to 5:95:0.1. The pure, product-containing fractions were combined and concentrated to give the title compound as the trifluoroacetate salt. MS: m/z=494 (M+1). HRMS: m/z=494.1999; calculated m/z=494.1987 for $C_{29}H_{25}FN_5O_2$.

Example 5

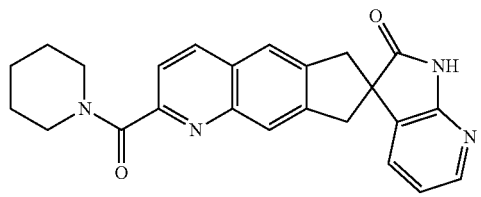 [SMILES: O=C(c1ccc2cc3c(cc2n1)CC1(C3)C(=O)Nc2ncccc21)N1CCCCC1]

(±)-2-(Piperidin-1-ylcarbonyl)-6,8-dihydrospiro[cyclopenta[g]quinoline-7,3'-pyrrolo[2,3-b]pyridin]-2'(1'H)-one A mixture of (±)-2'-oxo-1',2',6,8-tetrahydrospiro[cyclopenta[g]quinoline-7,3'-pyrrolo[2,3-b]pyridine]-2-carboxylic acid (15 mg, 0.045 mmol, described in Intermediate 12), piperidine (0.009 mL, 0.091 mmol), EDC (26 mg, 0.14 mmol), HOBT (21 mg, 0.14 mmol), and N,N-diisopropylethylamine (0.039 mL, 0.23 mmol) was stirred in DMF (1 mL) at ambient temperature for 18 h. The reaction mixture was purified directly by HPLC using a reversed phase C18 column and eluting with a gradient of $H_2O:CH_3CN:CF_3CO_2H$—90:10:0.1 to 5:95:0.1. The pure, product-containing fractions were combined and concentrated to give the title compound. MS: m/z=399 (M+1). HRMS: m/z=399.1817; calculated m/z—399.1816 for $C_{24}H_{22}N_4O_2$.

Example 6

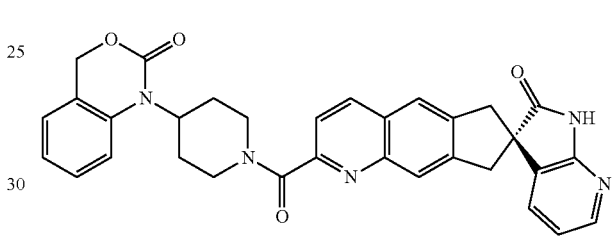

(7S)-2-{[4-(2-oxo-2H-3,1-benzoxazin-1(4H)-yl)piperidin-1-yl]carbonyl}-6,8-dihydrospiro[cyclopenta[g]quinoline-7,3'-pyrrolo[2,3-b]pyridin]-2'(1'H)-one A mixture of (S)-2'-oxo-1',2',6,8-tetrahydrospiro[cyclopenta[g]quinoline-7,3'-pyrrolo[2,3-b]pyridine]-2-carboxylic acid (15 mg, 0.045 mmol, described in Intermediate 9), 1-piperidin-4-yl-1,4-dihydro-2H-3,1-benzoxazin-2-one (12 mg, 0.045 mmol), EDC (10 mg, 0.050 mmol), HOIST (7 mg, 0.050 mmol), and N,N,N-triethylamine (0.006 mL, 0.045 mmol) was stirred in DMF (2.5 mL) at ambient temperature for 18 h. The reaction mixture was purified directly by HPLC using a reversed phase C18 column and eluting with a gradient of $H_2O:CH_3CN:CF_3CO_2H$—90:10:0.1 to 5:95:0.1. The pure, product-containing fractions were combined and concentrated to give the title compound. MS: m/z=546 (M+1). HRMS: m/z=546.2132; calculated m/z=546.2136 for $C_{32}H_{28}N_5O_4$.

Example 7

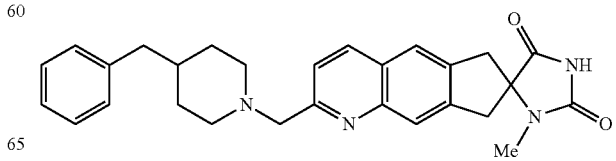

(±)-2-[(4-Benzylpiperidin-1-yl)methyl]-3'-methyl-6,
8-dihydro-2'H,5'H-spiro[cyclopenta[g]quinoline-7,
4'-imidazolidine]-2',5'-dione To a stirred solution of (±)-3'-methyl-2',5'-dioxo-6,8-dihydrospiro[cyclopenta[g]quinoline-7,4'-imidazolidine]-2-carbaldehyde (20 mg, 0.068 mmol, described in Intermediate 19) and 4-benzylpiperidine (18 mg, 0.10 mmol) in NMP (1 mL) was added resin bound sodium triacetoxyborohydride (4 mol equiv). After 18 h, the mixture was filtered and purified by HPLC using a reversed phase C18 column and eluting with a gradient of $H_2O:CH_3CN:CF_3CO_2H$—90:10:0.1 to 5:95:0.1. The pure, product-containing fractions were combined and concentrated to give the title compound as the trifluoroacetate salt. MS: m/z=455 (M+1). HRMS: m/z=455.2462; calculated m/z=455.2442 for $C_{28}H_{31}N_4O_2$.

Example 8

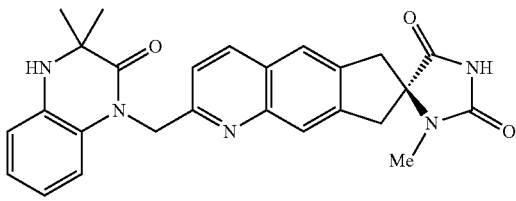 [SMILES: CN1C(=O)NC(=O)[C@]12Cc1cc3ccc(CN4C(=O)C(C)(C)Nc5ccccc54)nc3cc1C2]

(7R)-2-[(3,3-Dimethyl-2-oxo-3,4-dihydroquinoxalin-
1(2H)-yl)methyl]-3'-methyl-6,8-dihydro-2'H,5'H-
spiro[cyclopenta[g]quinoline-7,4'-imidazolidine]-2',
5'-dione To a solution of 3,3-dimethyl-3,4-dihydroquinoxalin-2 (1H)-one (56 mg, 0.32 mmol) in DMF (1 mL) at ambient temperature was added sodium hydride (13 mg, 0.32 mmol, 60% dispersion in mineral oil). The resulting mixture was stirred for 20 min, then (R)-2-(chloromethyl)-3'-methyl-6,8-dihydro-2'H,5'H-spiro[cyclopenta[g]quinoline-7,4'-imidazolidine]-2',5'-dione (20 mg, 0.063 mmol, described in Intermediate 18) was added and the resulting mixture was stirred at ambient temperature for 1 h. The reaction mixture was purified directly by HPLC using a reversed phase C18 column and eluting with a gradient of $H_2O:CH_3CN:CF_3CO_2H$—90:10:0.1 to 5:95:0.1. The pure, product-containing fractions were combined and concentrated to give the title compound as the trifluoroacetate salt. MS: m/z=456 (M+1). HRMS: m/z=456.2033; calculated m/z=456.2030 for $C_{26}H_{26}N_5O_3$.

Example 9

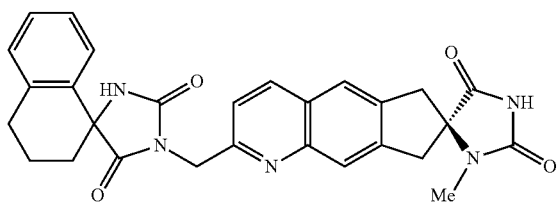 [SMILES: CN1C(=O)NC(=O)[C@]12Cc1cc3ccc(CN4C(=O)NC5(CCCc6ccccc65)C4=O)nc3cc1C2]

(7R)-2-[(2,5-Dioxo-3',4'-dihydro-1H,2'H-spiro[imi-
dazolidine-4,1'-naphthalen]-1-yl)methyl]-3'-methyl-
6,8-dihydro-2'H,5'H-spiro[cyclopenta[g]quinoline-7,
4'-imidazolidine]-2',5'-dione To a solution of (±)-3',4'-dihydro-2H,2'H,5H-spiro[imidazolidine-4,1'-naphthalene]-2,5-dione (14 mg, 0.063 mmol) and potassium carbonate (13 mg, 0.095 mmol) in DMF (1 mL), at ambient temperature, was added (R)-2-(chloromethyl)-3'-methyl-6,8-dihydro-2'H,5'H-spiro[cyclopenta[g] quinoline-7,4'-imidazolidine]-2',5'-dione (20 mg, 0.063 mmol, described in Intermediate 18). The resulting mixture was stirred at ambient temperature for 18 h. The reaction mixture was purified directly by HPLC using a reversed phase C18 column and eluting with a gradient of $H_2O:CH_3CN:CF_3CO_2H$—90:10:0.1 to 5:95:01. The pure, product-containing fractions were combined and concentrated to give the title compound as the trifluoroacetate salt. MS: m/z=496 (M+1). HRMS: m/z=496.1978; calculated m/z=496.1980 for $C_{28}H_{26}N_5O_4$.

Examples 10-19

Essentially following the procedures outlined for Example 1 the compounds listed in Table 2 were prepared. The requisite starting materials were commercially available, described in the literature, synthesized according to methodology described herein (vide supra), or readily synthesized by one skilled in the art of organic synthesis. In some cases, straightforward protecting group strategies were applied.

TABLE 2

| Example | $R^b$ | MS (M + 1) | Intermediate Amide |
|---|---|---|---|
| 10 | ![structure] | 385 | Commerically available |
| 11 | ![structure] | 494 | Commerically available |
| 12 | ![structure] | 475 | Milewska et. al., *Synthesis* 1996, 12, 1485-1488. |

TABLE 2-continued

| Example | R$^b$ | MS (M + 1) | Intermediate Amide |
|---|---|---|---|
| 13 | [3-methyl-3-phenyl-piperazin-2-one] | 490 | 27 |
| 14 | [3-benzyl-piperazin-2-one] | 490 | Commerically available |
| 15 | [3-(3-fluorobenzyl)-piperazin-2-one] | 507 | Commerically available |
| 16 | [3-benzyl-3-methyl-piperazin-2-one] | 504 | 43 |
| 17 | [3-benzyl-5,5-dimethyl-piperazin-2-one] | 518 | 41 |
| 18 | [3,3-dimethyl-3,4-dihydroquinoxalin-2(1H)-one] | 476 | Commerically available |
| 19 | [2H-benzo[b][1,4]oxazin-3(4H)-one] | 449 | Commerically available |

Examples 20-54

Essentially following the procedures outlined for Example 2 the compounds listed in Table 3 were prepared. The requisite amines were commercially available, described in the literature, synthesized according to methodology described herein (vide supra), or readily synthesized by one skilled in the art of organic synthesis. In some cases, straightforward protecting group strategies were applied.

TABLE 3

| Example | R$^b$ | MS (M + 1) | Intermediate Amine |
|---|---|---|---|
| 20 | [2-benzyl-octahydro-2,7-naphthyridine] | 544 | WO 2007/113596 |
| 21 | [spiro[indoline-3,4'-piperidine]] | 488 | Xie et. al., *Tetrahedron* 2004, 60(22), 4875-4878. |

TABLE 3-continued
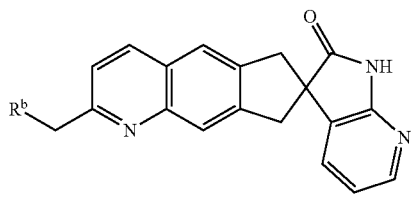
| Example | R<sup>b</sup> | MS (M + 1) | Intermediate Amine |
|---|---|---|---|
| 22 | 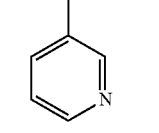 | 492 | FR 2911138, EP 532177 |
| 23 |  | 371 | Commercially available |
| 24 |  | 385 | Commercially available |
| 25 | 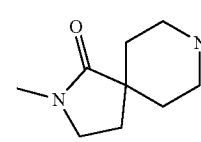 | 468 | Commercially available |
| 26 |  | 387 | Commercially available |
| 27 | 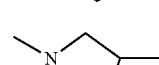 | 440 | Ohnmacht et. al., J. Heterocycl. Chem. 1983, 20, 321-329. |
| 28 | 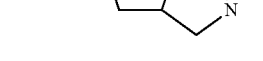 | 516 | Commercially available |
| 29 | 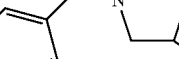 | 454 | Commercially available |
| 30 | 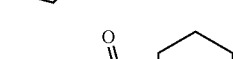 | 501 | Commercially available |
| 31 | 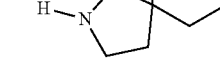 | 484 | Commercially available |

TABLE 3-continued

| Example | R$^b$ | MS (M + 1) | Intermediate Amine |
|---|---|---|---|
| 32 | | 566 | Commercially available |
| 33 | | 530 | Commercially available |
| 34 | | 502 | WO 2006/031610 |
| 35 | | 485 | WO 2003/106457 |
| 36 | | 486 | Commercially available |
| 37 | | 440 | Commercially available |
| 38 | | 544 | WO 2007/140383 |
| 39 | | 440 | WO 2007/113596 |

TABLE 3-continued

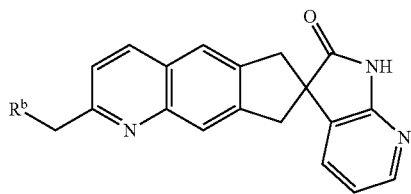

| Example | R$^b$ | MS (M + 1) | Intermediate Amine |
|---|---|---|---|
| 40 | (spiro diazacycle, HN-) | 440 | WO 2007/113596 |
| 41 | (spiro diazacycle, HN-) | 440 | WO 2007/113596 |
| 42 | (spiro indane-piperidine) | 487 | Commercially available |
| 43 | (spiro isobenzofuran-piperidine) | 489 | Commercially available |
| 44 | (4-phenylpiperazine) | 462 | Commercially available |
| 45 | (tetrahydro-β-carboline) | 472 | Commercially available |
| 46 | (spiro imidazolidinone-piperidine, N-phenyl) | 531 | Commercially available |
| 47 | (Boc-NH-piperidine) | 500 | Commercially available |
| 48 | (methoxycarbonylmethoxy-piperidine) | 473 | Commercially available |

TABLE 3-continued

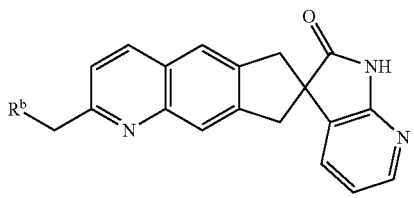

| Example | R$^b$ | MS (M + 1) | Intermediate Amine |
|---|---|---|---|
| 49 | | 485 | Commercially available |
| 50 | | 531 | WO 2006/041830 |
| 51 | | 401 | Commercially available |
| 52 | | 400 | Commercially available |
| 53 | | 507 | Commercially available |
| 54 | | 519 | WO 2006/041830 |

Examples 55-100

Essentially following the procedures outlined for Example 3 the compounds listed in Table 4 were prepared. The requisite starting materials were commercially available, described in the literature, synthesized according to methodology described herein (vide supra), or readily synthesized by one skilled in the art of organic synthesis. In some cases, straightforward protecting group strategies were applied.

TABLE 4

| Example | R<sup>b</sup> | MS (M + 1) | Intermediate Amine |
|---|---|---|---|
| 55 | spiro[cyclopentane-indanyl-piperazinone] | 556 | 23 |
| 56 | 3-phenyl-hexahydropyrrolo[1,2-a]pyrazin-1-one | 516 | 24 |
| 57 | 3-phenyl-hexahydropyrrolo[1,2-a]pyrazin-1-one (enantiomer) | 516 | 25 |
| 58 | 3-(4-fluorophenyl)-piperazin-2-one | 494 | Commercially available |
| 59 | 3-phenyl-piperazin-2-one | 576 | Commercially available |

TABLE 4-continued

| Example | R<sup>b</sup> | MS (M + 1) | Intermediate Amine |
|---|---|---|---|
| 60 | piperazin-2-one | 400 | Commercially available |
| 61 | tert-butyl 2-phenylpiperazine-1-carboxylate | 562 | Commercially available |
| 62 | tert-butyl 3-phenylpiperazine-1-carboxylate | 562 | Commercially available |
| 63 | 2-phenylpiperazine | 462 | Commercially available |
| 64 | 2-phenylpiperazine | 462 | Commercially available |
| 65 | 3-ethyl-3-phenyl-piperazin-2-one | 504 | 26 |

TABLE 4-continued

| Example | R^b | MS (M + 1) | Intermediate Amine |
|---|---|---|---|
| 66 | (ethyl ester-CH2-piperazinone with 4-fluorophenyl) | 580 | 49 |
| 67 | (methyl, phenyl-piperazinone) | 490 | 27 |
| 68 | (tetrahydronaphthalene-spiro-piperazinone) | 516 | 44 |
| 69 | (cyclopentane-spiro-phenyl-piperazinone) | 530 | 28 |
| 70 | (indane-spiro-piperazinone) | 502 | 45 |
| 71 | (isobutyl-piperazinone) | 456 | Commercially available |
| 72 | (Boc-piperazine) | 486 | Commercially available |
| 73 | (Boc-diphenyl-piperazine) | 638 | Commercially available |
| 74 | (N-methyl-phenyl-piperazine) | 476 | Commercially available |
| 75 | (N-methyl-phenyl-piperazine) | 476 | Commercially available |
| 76 | (piperazine) | 386 | Commercially available |

TABLE 4-continued

| Example | R^b | MS (M + 1) | Intermediate Amine |
|---|---|---|---|
| 77 | (HN-piperazine with two phenyl substituents) | 538 | Commercially available |
| 78 | (spiro cyclopentyl piperazinone) | 566 | 46 |
| 79 | (3-methyl piperazinone) | 414 | Commercially available |
| 80 | (3-(2-methyl-4-fluorophenyl) piperazinone) | 508 | WO 2008/090117 |
| 81 | (gem-dimethyl piperazinone) | 428 | Commercially available |
| 82 | (2-phenyl piperazine) | 461 | Commercially available |
| 83 | (1-phenyl-tetrahydropyrrolo[1,2-a]pyrazine) | 498 | Commercially available |
| 84 | (benzyl piperazinone, phenyl) | 566 | 29 |
| 85 | (benzyl piperazinone, phenyl) | 566 | 30 |
| 86 | (methyl-phenyl piperazinone) | 490 | 31 |

TABLE 4-continued

| Example | R^b | MS (M + 1) | Intermediate Amine |
|---|---|---|---|
| 87 | (spiro[4.4] piperazinone with benzyl) | 544 | 22 |
| 88 | (spiro[4.4] piperazinone with benzyl, stereo) | 544 | 32 |
| 89 | (spiro[4.4] piperazinone with benzyl, stereo) | 544 | 33 |
| 90 | (spiro[4.4] piperazinone) | 454 | 34 |
| 91 | (piperazinone with CH2OH and phenyl) | 506 | 35 |
| 92 | (spiro[4.4] piperazinone with phenethyl) | 558 | 36 |
| 93 | (spiro[4.4] piperazinone with 1-phenylethyl) | 558 | 37 |
| 94 | (spiro[4.4] piperazinone with 2-phenylpropan-2-yl) | 572 | 38 |
| 95 | (spiro[4.4] piperazinone with methyl and benzyl) | 558 | 39 |

TABLE 4-continued

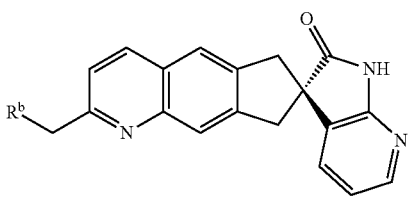

| Example | $R^b$ | MS (M + 1) | Intermediate Amine |
|---|---|---|---|
| 96 | 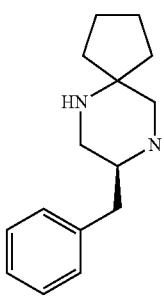 | 518 | 40 |
| 97 | 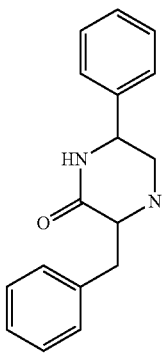 | 530 | 47 |
| 98 | (structure) | 566 | 42 |
| 99 | 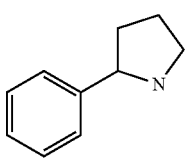 | 447 | Commercially available |

TABLE 4-continued

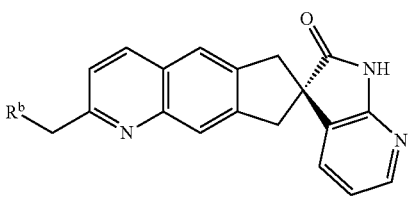

| Example | $R^b$ | MS (M + 1) | Intermediate Amine |
|---|---|---|---|
| 100 | (benzoxazole-diazepane) | 517 | Commercially available |

Example 101

Essentially following the procedures outlined for Example 4 the compound listed in Table 5 was prepared. The requisite starting materials were commercially available, described in the literature, synthesized according to methodology described herein (vide supra), or readily synthesized by one skilled in the art of organic synthesis. In some cases, straightforward protecting group strategies were applied.

TABLE 5

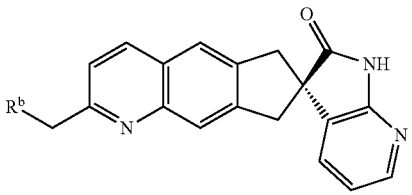

| Example | $R^b$ | MS (M + 1) |
|---|---|---|
| 101 | (piperazinone-phenyl) | 576 |

Examples 102-127

Essentially following the procedures outlined for Example 5 the compounds listed in Table 6 were prepared. The requisite amines were commercially available, described in the literature, synthesized according to methodology described herein (vide supra), or readily synthesized by one skilled in the art of organic synthesis. In some cases, straightforward protecting group strategies were applied.

TABLE 6
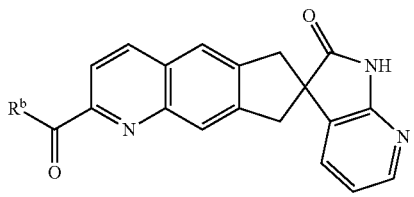
| Example | R<sup>b</sup> | MS (M + 1) | Intermediate Amine |
|---|---|---|---|
| 102 | | 513 | Commercially available |
| 103 | | 516 | Commercially available |
| 104 | | 438 | Tomita et. al., *J. Med. Chem.* 2002, 45(25), 5564-5575. |
| 105 | | 503 | Commercially available |
| 106 | | 457 | Commercially available |
| 107 | | 491 | Commercially available |
| 108 | | 442 | Commercially available |
| 109 | | 519 | Commercially available |

TABLE 6-continued

| Example | R^b | MS (M + 1) | Intermediate Amine |
|---|---|---|---|
| 110 | | 530 | Commercially available |
| 111 | | 531 | Commercially available |
| 112 | | 531 | WO 2004/014851 |
| 113 | | 484 | Commercially available |
| 114 | | 517 | Commercially available |
| 115 | | 503 | Commercially available |
| 116 | | 489 | Commercially available |
| 117 | | 463 | Grunewald et. al., *J. Med. Chem.* 1996, 39(18), 3539-3546. |

TABLE 6-continued

| Example | R$^b$ | MS (M + 1) | Intermediate Amine |
|---|---|---|---|
| 118 | | 519 | Commercially available |
| 119 | | 506 | FR 2911138, EP 532177 |
| 120 | | 385 | Commercially available |
| 121 | | 558 | Commercially available |
| 122 | | 529 | Yamada et. al., *Eur. J. Med. Chem. Chim. Ther.* 1983, 18(3), 209-214. |
| 123 | | 545 | Commercially available |
| 124 | | 437 | Commercially available |

TABLE 6-continued

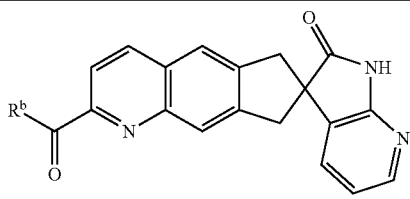

| Example | $R^b$ | MS (M + 1) | Intermediate Amine |
|---|---|---|---|
| 125 | 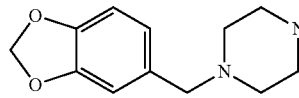 | 534 | Commercially available |
| 126 | 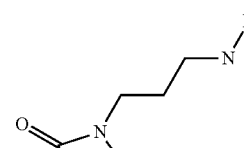 | 456 | Commercially available |
| 127 | 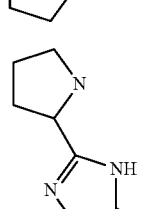 | 468 | Commercially available |

Example 128

Essentially following the procedures outlined for Example 6 the compound listed in Table 7 was prepared. The requisite amines were commercially available, described in the literature, synthesized according to methodology described herein (vide supra), or readily synthesized by one skilled in the art of organic synthesis. In some cases, straightforward protecting group strategies were applied.

Examples 129-209

Essentially following the procedures outlined for Example 7 the compounds listed in Table 8 were prepared. The requisite starting materials were commercially available, described in the literature, synthesized according to methodology described herein (vide supra), or readily synthesized by one skilled in the art of organic synthesis. In some cases, straightforward protecting group strategies were applied.

TABLE 7

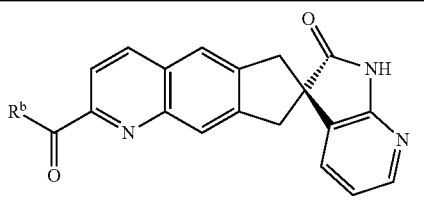

| Example | $R^b$ | MS (M + 1) |
|---|---|---|
| 128 | 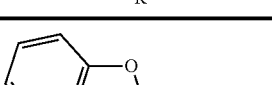 | 531 |

TABLE 8
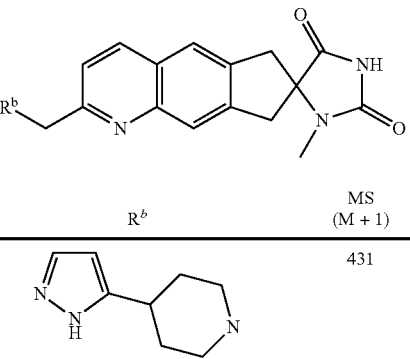
| Example | R$^b$ | MS (M + 1) | Intermediate Amine |
|---|---|---|---|
| 129 | 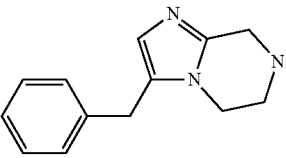 | 431 | WO 2006/048750 |
| 130 | 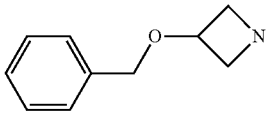 | 493 | Hamblett et. al., *Bioorg. Med. Chem. Lett.* 2007, 17(19), 5300-5309. |
| 131 | 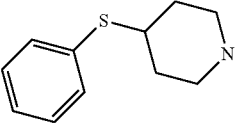 | 443 | Falgueyret et. al., *J. Med. Chem.* 2001, 44(1), 94-104. |
| 132 | 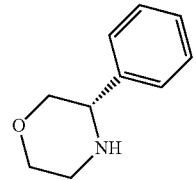 | 473 | Commerically available |
| 133 | 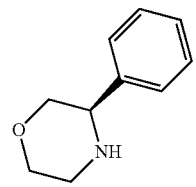 | 443 | Commerically available |
| 134 | 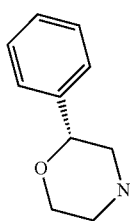 | 443 | Commerically available |
| 135 | 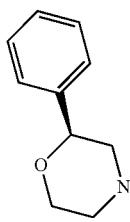 | 443 | Commerically available |
| 136 | | 443 | Commerically available |

TABLE 8-continued

| Example | R$^b$ | MS (M + 1) | Intermediate Amine |
|---|---|---|---|
| 137 | | 485 | Commerically available |
| 138 | | 477 | Commerically available |
| 139 | | 481 | Commerically available |
| 140 | | 486 | Commerically available |
| 141 | | 436 | Commerically available |
| 142 | | 482 | Filosa et. al., *Eur. J. Med. Chem. Chim. Ther.* 2007, 42(3), 293-306. |
| 143 | | 456 | Commerically available |

TABLE 8-continued
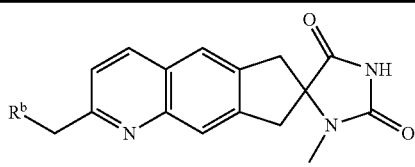
| Example | R$^b$ | MS (M + 1) | Intermediate Amine |
|---|---|---|---|
| 144 | | 469 | Commerically available |
| 145 | | 433 | WO 2004/094371 |
| 146 | | 472 | JP 03118380 |
| 147 | | 455 | Commerically available |
| 148 | | 482 | Commerically available |
| 149 | | 484 | International Electronic Conferences on Synthetic Organic Chemistry, 5th, 6th, Sept. 1-30, 2001 and 2002 and 7th, 8th, Nov. 1-30, 2003 and 2004, 682-688 |
| 150 | | 457 | Commerically available |
| 151 | | 403 | Commerically available |
| 152 | | 429 | Grunewald et. al., *J. Med. Chem.* 1996, 39(18), 3539-3546. |

TABLE 8-continued
| Example | R$^b$ | MS (M + 1) | Intermediate Amine |
|---|---|---|---|
| 153 | 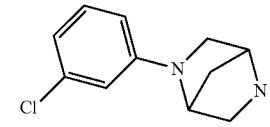 | 543 | Commerically available |
| 154 | 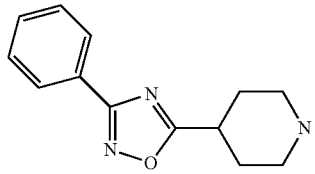 | 489 | Commerically available |
| 155 | 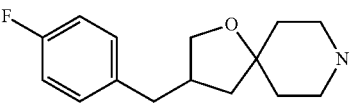 | 510 | Commerically available |
| 156 | 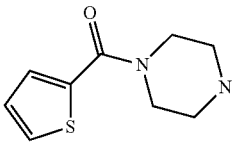 | 529 | Commerically available |
| 157 | 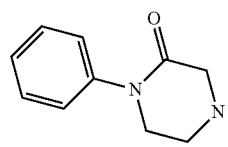 | 476 | Commerically available |
| 158 | 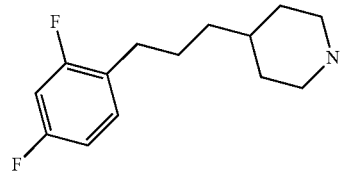 | 456 | Commerically available |
| 159 | 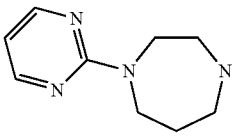 | 519 | WO 2000/059503 |
| 160 | 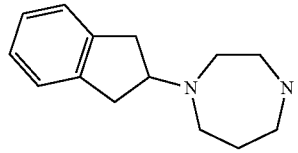 | 458 | Commerically available |
| 161 |  | 496 | Commerically available |

TABLE 8-continued

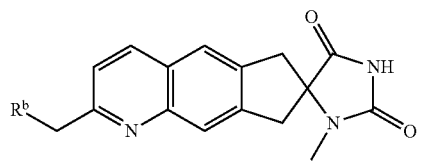

| Example | R$^b$ | MS (M + 1) | Intermediate Amine |
|---|---|---|---|
| 162 | (indol-3-ylmethyl piperazine) | 495 | Mutulis et. al., *Bioorg. Med. Cheml Lett.* 2002, 12(7), 1035-1038. |
| 163 | (2-pyrrolidinyl indole) | 466 | Commerically available |
| 164 | (4-methylphenethyl piperidine) | 483 | Commerically available |
| 165 | (4-hydroxy-4-(3-phenylpropyl)piperidine) | 499 | Chenard et. al., *J. Med. Chem.* 1995, 38(16), 3138-3145. |
| 166 | (indol-6-yl carbonyl piperazine) | 509 | Commerically available |
| 167 | (cyclopropyl(phenylsulfonyl)methyl piperidine) | 560 | Commerically available |
| 168 | (tetrazol-2-yl piperidine) | 433 | WO 2004/094371 |
| 169 | (benzyl diazabicyclo carbamate) | 512 | Commerically available |

TABLE 8-continued

| Example | R$^b$ | MS (M + 1) | Intermediate Amine |
|---|---|---|---|
| 170 | | 512 | Commerically available |
| 171 | | 497 | Commerically available |
| 172 | | 439 | Commerically available |
| 173 | | 439 | Commerically available |
| 174 | | 435 | Yamade et. at., *Eur. J. Med. Chem. Chim. Ther.* 1983, 18(3), 209-214. |
| 175 | | 440 | Commerically available |
| 176 | | 510 | Commerically available |

TABLE 8-continued

[Structure shown: spiro compound with Rb substituent, pyridine-fused cyclopentane, and N-methyl hydantoin]

| Example | R$^b$ | MS (M + 1) | Intermediate Amine |
|---------|-------|------------|---------------------|
| 177 | [benzoyl-piperazinyl-ethylamine] | 513 | Schaus et. al., J. Med. Chem. 1998, 41(11), 1943-1955. |
| 178 | [5-phenyl-1H-1,2,3-triazol-1-yl-ethylamine] | 468 | Commerically available |
| 179 | [(3-methylpyridin-2-yl)methyl-pyrrolidine] | 456 | Commerically available |
| 180 | [2-phenylpyrrolidine] | 427 | Commerically available |
| 181 | [2-(4-fluorophenyl)azetidine] | 431 | Commerically available |
| 182 | [2-(2-phenylethyl)pyrrolidine] | 455 | Commerically available |
| 183 | [3-(pyridin-2-ylmethoxy)piperidine] | 471 | Commerically available |
| 184 | [(S)-2-isopropyl-4-methylpiperazine] | 422 | Commerically available |
| 185 | [piperazin-2-one] | 380 | Commerically available |

TABLE 8-continued
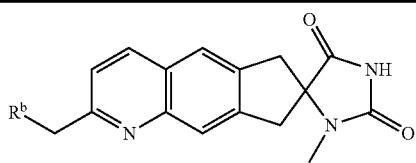
| Example | R$^b$ | MS (M + 1) | Intermediate Amine |
|---|---|---|---|
| 186 | | 434 | Brill, Schultz, *J. Org. Chem.* 1963, 28, 1135, 1137. |
| 187 | | 505 | Commerically available |
| 188 | | 394 | Commerically available |
| 189 | | 408 | Commerically available |
| 190 | | 512 | Commerically available |
| 191 | | 456 | Commerically available |
| 192 | | 408 | Commerically available |

TABLE 8-continued

| Example | R$^b$ | MS (M + 1) | Intermediate Amine |
|---|---|---|---|
| 193 | | 394 | Commerically available |
| 194 | | 490 | Saari et. al., J. Med. Chem. 1990, 33(9), 2590-2595. |
| 195 | | 532 | Commerically available |
| 196 | | 466 | Commerically available |
| 197 | | 502 | WO 9716446 |
| 198 | | 394 | Commerically available |
| 199 | | 474 | Commerically available |

TABLE 8-continued
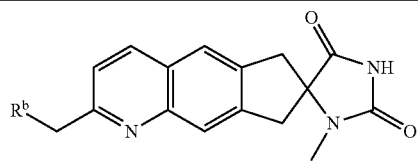
| Example | R$^b$ | MS (M + 1) | Intermediate Amine |
|---|---|---|---|
| 200 | | 422 | Commerically available |
| 201 | | 474 | Commerically available |
| 202 | | 442 | Commerically available |
| 203 | | 442 | Commerically available |
| 204 | | 438 | Commerically available |
| 205 | | 482 | WO 2007/113596 |
| 206 | | 499 | Commerically available |

TABLE 8-continued

| Example | R$^b$ | MS (M + 1) | Intermediate Amine |
|---------|-------|------------|--------------------|
| 207 | [ethyl 4-fluoropiperidine-4-carboxylate structure] | 455 | WO 2008/011130 |
| 208 | [imidazo[4,5-b]pyridin-2(3H)-one piperidinyl structure] | 498 | Burgey et. al., *Bioorg. Med. Chem. Lett.* 2006, 16(19), 5052-5056. |
| 209 | [imidazol-1-ylmethyl piperidine structure] | 445 | WO 2007/113596 |

Examples 210-212

Essentially following the procedures outlined for Example 8 the compounds listed in Table 9 were prepared. The requisite starting materials were commercially available, described in the literature, synthesized according to methodology described herein (vide supra), or readily synthesized by one skilled in the art of organic synthesis. In some cases, straightforward protecting group strategies were applied.

TABLE 9

| Example | R$^b$ | MS (M + 1) | Intermediate Amide |
|---------|-------|------------|--------------------|
| 210 | [spiro cyclopentane piperazinone with 3,5-difluorophenyl structure] | 546 | WO 2008/020902 |
| 211 | [3-(4-fluorophenyl)piperazin-2-one structure] | 474 | Commercially available |
| 212 | [pyrrolidinyl-benzimidazole with fluorophenyl structure] | 538 | 50 |

The utility of the compounds in accordance with the present invention as antagonists of CGRP receptor activity may be demonstrated by methodology known in the art. Inhibition of the binding of $^{125}$I-CGRP to receptors and functional antagonism of CGRP receptors were determined as follows:

NATIVE RECEPTOR BINDING ASSAY: The binding of $^{125}$I-CGRP to receptors in SK-N-MC cell membranes was carried out essentially as described (Edvinsson et al. (2001) *Eur. J. Pharmacol.* 415, 39-44). Briefly, membranes (25 μg) were incubated in 1 mL of binding buffer [10 mM HEPES, pH 7.4, 5 mM MgCl$_2$ and 0.2% bovine serum albumin (BSA)] containing 10 pM $^{125}$I-CGRP and antagonist. After incubation at room temperature for 3 h, the assay was terminated by filtration through GFB glass fibre filter plates (PerkinElmer) that had been blocked with 0.5% polyethyleneimine for 3 h. The filters were washed three times with ice-cold assay buffer (10 mM HEPES, pH 7.4 and 5 mM MgCl$_2$), then the plates were air dried. Scintillation fluid (50 μL) was added and the radioactivity was counted on a Topcount (Packard Instrument). Data analysis was carried out by using Prism and the K$_i$ was determined by using the Cheng-Prusoff equation (Cheng & Prusoff (1973) *Biochem. Pharmacol.* 22, 3099-3108).

RECOMBINANT RECEPTOR: Human CL receptor (Genbank accession number L76380) was subcloned into the expression vector pIREShyg2 (BD Biosciences Clontech) as a 5'NheI and 3' PmeI fragment. Human RAMP 1 (Genbank accession number AJ001014) was subcloned into the expression vector pIRESpuro2 (BD Biosciences Clontech) as a 5'NheI and 3'NotI fragment. HEK 293 cells (human embryonic kidney cells; ATCC #CRL-1573) were cultured in DMEM with 4.5 g/L glucose, 1 mM sodium pyruvate and 2 mM glutamine supplemented with 10% fetal bovine serum (FBS), 100 units/mL penicillin and 100 μg/mL streptomycin, and maintained at 37° C. and 95% humidity. Cells were subcultured by treatment with 0.25% trypsin with 0.1% EDTA in HBSS. Stable cell line generation was accomplished by co-transfecting 10 μg of DNA with 30 μg Lipofectamine 2000 (Invitrogen) in 75 cm$^2$ flasks. CL receptor and RAMP1 expression constructs were co-transfected in equal amounts. Twenty-four hours after transfection the cells were diluted and selective medium (growth medium+300 μg/mL hygromycin and 1 μg/mL puromycin) was added the following day. A clonal cell line was generated by single cell deposition utilizing a FACS Vantage SE (Becton Dickinson). Growth medium was adjusted to 150 μg/mL hygromycin and 0.5 μg/mL puromycin for cell propagation.

RECOMBINANT RECEPTOR BINDING ASSAY: Cells expressing recombinant human CL receptor/RAMP1 were washed with PBS and harvested in harvest buffer containing 50 mM HEPES, 1 mM EDTA and Complete protease inhibitors (Roche). The cell suspension was disrupted with a laboratory homogenizer and centrifuged at 48,000 g to isolate membranes. The pellets were resuspended in harvest buffer plus 250 mM sucrose and stored at −70° C. For binding assays, 20 μg of membranes were incubated in 1 ml binding buffer (10 mM HEPES, pH 7.4, 5 mM MgCl$_2$, and 0.2% BSA) for 3 hours at room temperature containing 10 pM $^{125}$I-hCGRP (GE Healthcare) and antagonist. The assay was terminated by filtration through 96-well GFB glass fiber filter plates (PerkinElmer) that had been blocked with 0.05% polyethyleneimine. The filters were washed 3 times with ice-cold assay buffer (10 mM HEPES, pH 7.4 and 5 mM MgCl$_2$). Scintillation fluid was added and the plates were counted on a Topcount (Packard). Non-specific binding was determined and the data analysis was carried out with the apparent dissociation constant (K$_i$) determined by using a non-linear least squares fitting the bound CPM data to the equation below:

$$Y_{obsd} = \frac{(Y_{max} - Y_{min})(\%\,I_{max} - \%\,I_{min}/100) + Y_{min} + (Y_{max} - Y_{min})(100 - \%\,I_{max}/100)}{(1 + ([Drug]/K_i(1 + [Radiolabel]/K_d)^{nH})}$$

Where Y is observed CPM bound, $Y_{max}$ is total bound counts, $Y_{min}$ is non specific bound counts, ($Y_{max}$-$Y_{min}$) is specific bound counts, % $I_{max}$ is the maximum percent inhibition, % I min is the minimum percent inhibition, radiolabel is the probe, and the K$_d$ is the apparent dissociation constant for the radioligand for the receptor as determined by Hot saturation experiments.

RECOMBINANT RECEPTOR FUNCTIONAL ASSAY: Cells were plated in complete growth medium at 85,000 cells/well in 96-well poly-D-lysine coated plates (Corning) and cultured for ~19 h before assay. Cells were washed with PBS and then incubated with inhibitor for 30 min at 37° C. and 95% humidity in Cellgro Complete Serum-Free/Low-Protein medium (Mediatech, Inc.) with L-glutamine and 1 g/L BSA. Isobutyl-methylxanthine was added to the cells at a concentration of 300 μM and incubated for 30 min at 37° C. Human α-CGRP was added to the cells at a concentration of 0.3 nM and allowed to incubate at 37° C. for 5 mM. After α-CGRP stimulation the cells were washed with PBS and processed for cAMP determination utilizing the two-stage assay procedure according to the manufacturer's recommended protocol (cAMP SPA direct screening assay system; RPA 559; GE Healthcare). Dose response curves were plotted and IC$_{50}$ values determined from a 4-parameter logistic fit as defined by the equation y=((a−d)/(1+(x/e)$^b$) d, where y=response, x=dose, a=max response, d=min response, c=inflection point and b=slope.

The compounds of the invention were tested according to the foregoing recombinant receptor binding assay, and typically had activity as antagonists of the CGRP receptor in the aforementioned assays, with a K$_i$ value of less than 50,000 nM.

Examplary K$_i$ values in the recombinant receptor binding assay for exemplary compounds of the invention are provided in the table below:

| Example | Ki (nM) |
|---|---|
| 3 | 0.77 |
| 11 | 1.8 |
| 19 | 2.9 |
| 87 | 0.34 |
| 64 | 6.6 |
| 95 | 17 |
| 84 | 0.72 |
| 8 | 35 |
| 88 | 2.6 |
| 76 | 0.73 |
| 69 | 43 |
| 61 | 58 |
| 27 | 150 |
| 184 | 1700 |
| 147 | 1100 |
| 7 | 3800 |
| 45 | 180 |
| 115 | 7400 |
| 19 | 4.2 |
| 114 | 15000 |
| 209 | 85 |

The following abbreviations are used throughout the text:
Me: methyl
Et: ethyl
t-Bu: tert-butyl
Bu: butyl
iPr: isopropyl
Ar: aryl
Ph: phenyl
Bn: benzyl
Py: pyridyl
Ac: acetylate
OAc: acetate
DCE: dichloroethene
TFA: trifluoroacetic acid
TEA: triethlamine
BOC: t-butyloxycarbonyl
BOP: Benzotriazole-1-yl-oxy-tris-(dimethylamino)-phosphonium hexafluorophosphate
DIEA: N,N-Diisopropyl-ethylamine
HOBT: 1-Hydroxybenzotriazole
EDC: 1-Ethyl-3-(3-dimethyllaminopropyl)carbodiimide
PyCIU: chlorodipyrrolidinocarbenium
n-BuLi: n-butyllithium
HATU: 2-(1H-7-Azabenzotriazol-1-yl)-1,1,3,3-tetramethyl uronium hexafluorophosphate methanaminium
EDTA: Ethylenediaminetetracetic acid
DMF: dimethylformamide
HMDS: hexamethyldisilazane
THF: tetrahydrofuran
DMSO: dimethylsulfoxide
SEMCl: 2-trimethylsilylethyoxymethyl chloride
PBPB: pyridinium bromide perbromide
DMEM: Dulbecco's Modified Eagle Medium (High Glucose)
FBS: fetal bovine serum
BSA: bovine serum albumin
PBS: phosphate-buffered saline
HEPES: N-(2-Hydroxyethyppiperazine-N'-2-ethane-sulfonic Acid
rt: room temperature
min: minutes
h: hours
aq: aqueous
HPLC: high performance liquid chromatography
LCMS: liquid chromatography-mass spectrometry While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. The following compounds:

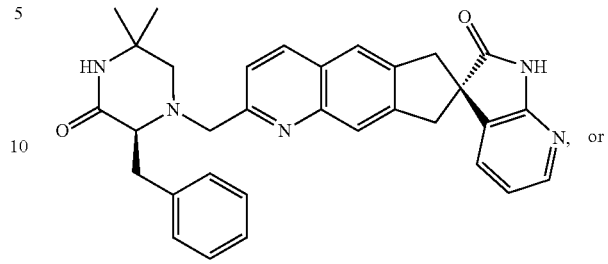

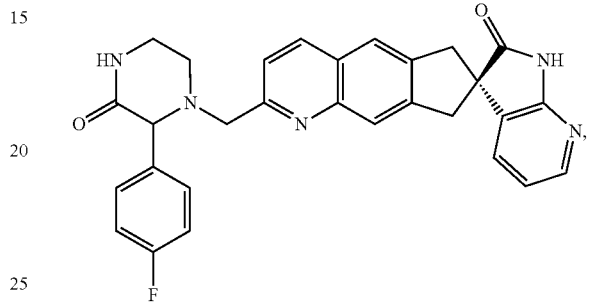

or a pharmaceutically acceptable salt thereof.

2. A compound of formula (VA)

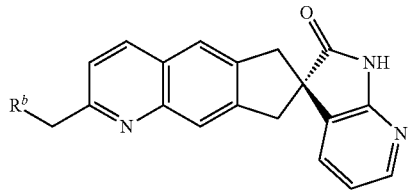

(VA)

wherein $R^b$ is attached via the sub-valent N of the group selected from the group consisting of

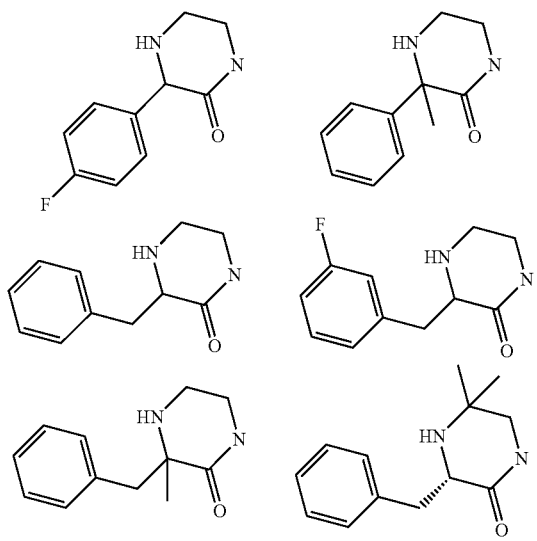

123
-continued
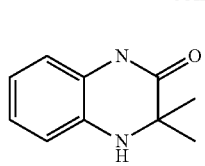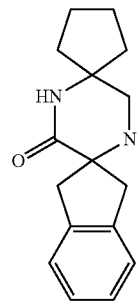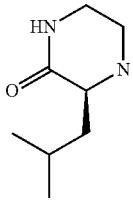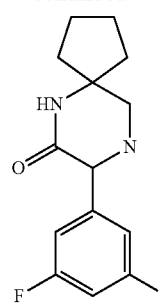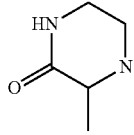
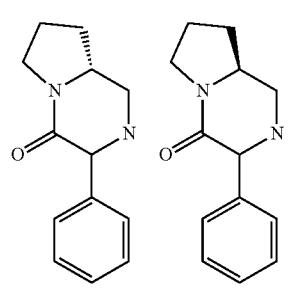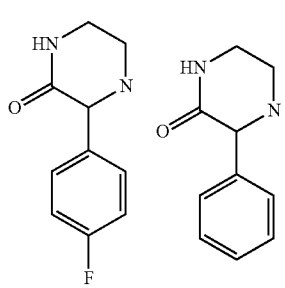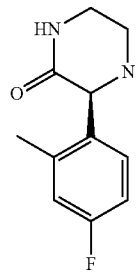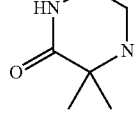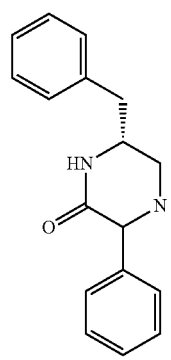
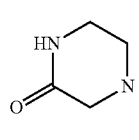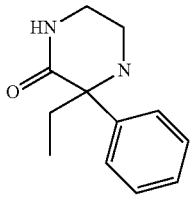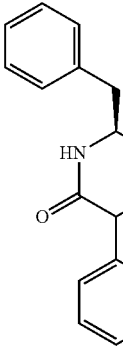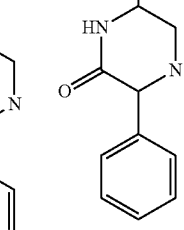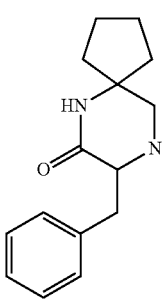
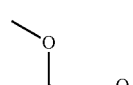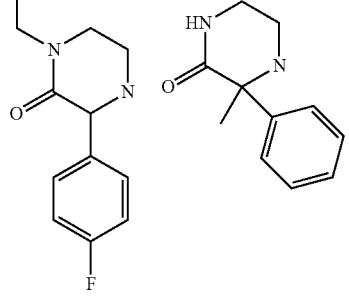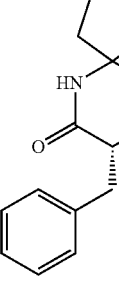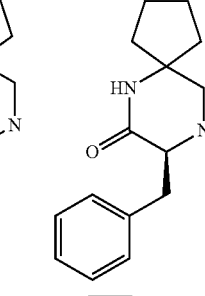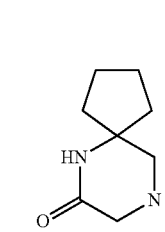
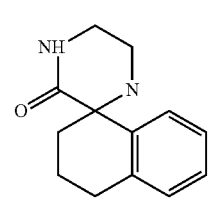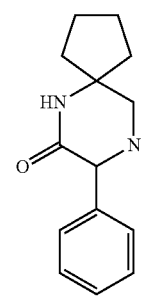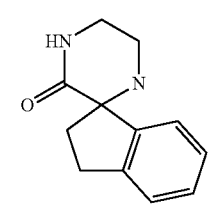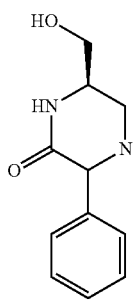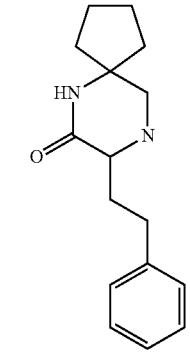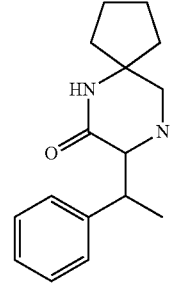
124
-continued -continued
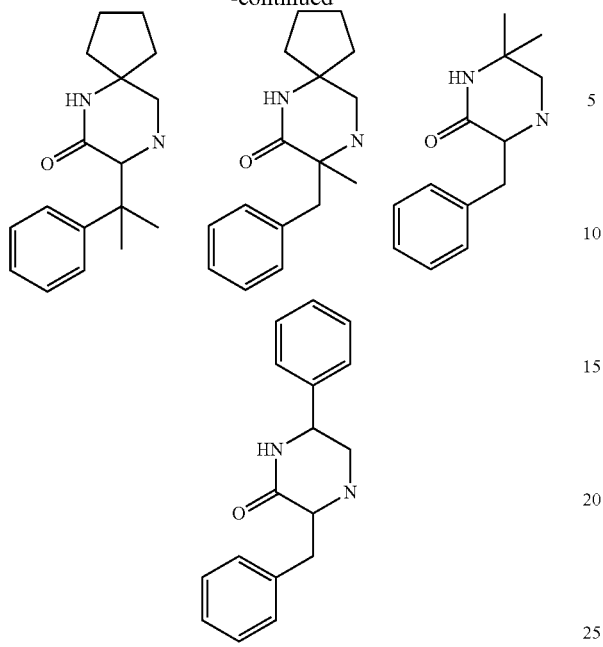
or a pharmaceutically acceptable salt thereof.
3. A pharmaceutical composition which comprises an inert carrier and the compound of claim 2, or a pharmaceutically acceptable salt thereof.
* * * * *